United States Patent
Magnin et al.

(10) Patent No.: US 10,588,611 B2
(45) Date of Patent: Mar. 17, 2020

(54) IMPLANT RETENTION ATTACHMENT AND METHOD OF USE

(71) Applicant: DC DEVICES, INC., Tewksbury, MA (US)

(72) Inventors: Christopher J. Magnin, Andover, MA (US); Matthew J. Finch, Somerville, MA (US); Hiroatsu Sugimoto, Cambridge, MA (US); Stephen J. Forcucci, Winchester, MA (US)

(73) Assignee: Corvia Medical Inc., Tewskbury, MA (US)

( * ) Notice: Subject to any disclaimer, the term of this patent is extended or adjusted under 35 U.S.C. 154(b) by 641 days.

(21) Appl. No.: 13/867,003

(22) Filed: Apr. 19, 2013

(65) Prior Publication Data

US 2013/0281988 A1    Oct. 24, 2013

Related U.S. Application Data

(60) Provisional application No. 61/635,842, filed on Apr. 19, 2012.

(51) Int. Cl.
*A61B 17/00* (2006.01)
*A61M 27/00* (2006.01)

(52) U.S. Cl.
CPC .... *A61B 17/00234* (2013.01); *A61B 17/0057* (2013.01); *A61M 27/002* (2013.01);
(Continued)

(58) Field of Classification Search
CPC ............... A61F 2/95; A61F 2002/9505; A61F 2002/9511; A61F 2002/9528; A61F 2/962;
(Continued)

(56) References Cited

U.S. PATENT DOCUMENTS

| 4,018,228 A | 4/1977 | Goosen |
| 4,705,507 A | 11/1987 | Boyles |

(Continued)

FOREIGN PATENT DOCUMENTS

| EP | 1470785 | 10/2004 |
| EP | 2537490 | 12/2012 |

(Continued)

OTHER PUBLICATIONS

Ad et al., "A one way valved atrial septal patch: A new surgical techniques and its clinical applicaiton", The Journal of Thoracic and Cardiovascular Surgery, vol. 111, Apr. 1996, pp. 841-848.
(Continued)

*Primary Examiner* — Ryan J. Severson
*Assistant Examiner* — Mohamed G Gabr
(74) *Attorney, Agent, or Firm* — Helen S. Liu

(57) ABSTRACT

The present teachings generally relate a delivery system having an implant retention mechanism. Specifically, the delivery system includes a delivery sheath, a delivery catheter, and a flexible or a rigid implant retention mechanism. The flexible implant retention mechanism includes an implant retention string having a fixed end and a free end where the free end extends from the fixed end, crosses a retention outlet of an implant, and extends proximally through a lumen of the delivery sheath. The rigid implant retention mechanism includes an implant retention wire having a fixed end and a free end where the free end extends from the fixed end, crosses a retention outlet of an implant, and extends proximally through a lumen of the delivery sheath.

7 Claims, 10 Drawing Sheets

(52) U.S. Cl.
CPC .............. *A61B 2017/00575* (2013.01); *A61B 2017/00584* (2013.01); *A61B 2017/00592* (2013.01); *A61B 2017/00606* (2013.01); *A61B 2017/00623* (2013.01)

(58) Field of Classification Search
CPC .... A61F 2/966; A61F 2002/9665; A61F 2/01; A61F 2002/011; A61F 2002/9517; A61F 2002/018; A61F 2230/005; A61F 2230/008; A61F 2230/0067; A61M 27/002; A61M 25/01; A61B 17/0057; A61B 17/221; A61B 17/32056; A61B 17/00234; A61B 2017/00575; A61B 2017/00585; A61B 2017/00592; A61B 2017/00606; A61B 2017/00623
See application file for complete search history.

(56) References Cited

U.S. PATENT DOCUMENTS

| | | | |
|---|---|---|---|
| 5,108,420 A | | 4/1992 | Marks |
| 5,171,233 A | | 12/1992 | Amplatz et al. |
| 5,334,217 A | | 8/1994 | Das |
| 5,387,219 A | * | 2/1995 | Rappe ................ A61B 17/1214 606/1 |
| 5,429,144 A | | 7/1995 | Wilk |
| 5,578,045 A | | 11/1996 | Das |
| 5,693,090 A | | 12/1997 | Unsworth et al. |
| 5,702,412 A | | 12/1997 | Popov et al. |
| 5,725,552 A | | 3/1998 | Kotula et al. |
| 5,824,071 A | | 10/1998 | Nelson et al. |
| 5,876,436 A | | 3/1999 | Vanney et al. |
| 5,911,725 A | * | 6/1999 | Boury .................... A61B 17/22 606/108 |
| 6,050,936 A | | 4/2000 | Schweich et al. |
| 6,077,281 A | | 6/2000 | Das |
| 6,123,715 A | | 9/2000 | Amplatz |
| 6,156,055 A | | 12/2000 | Ravenscroft |
| 6,190,353 B1 | | 2/2001 | Makower et al. |
| 6,193,734 B1 | | 2/2001 | Bolduc |
| 6,258,119 B1 | | 7/2001 | Hussein et al. |
| 6,334,864 B1 | | 1/2002 | Amplatz et al. |
| 6,350,277 B1 | | 2/2002 | Kocur |
| 6,355,050 B1 | | 3/2002 | Pinheiro |
| 6,355,052 B1 | | 3/2002 | Neuss et al. |
| 6,383,195 B1 | | 5/2002 | Richard |
| 6,395,017 B1 | | 5/2002 | Dwyer |
| 6,402,777 B1 | | 6/2002 | Globerman et al. |
| 6,409,716 B1 | | 6/2002 | Sahatjian et al. |
| 6,440,152 B1 | | 8/2002 | Gainor et al. |
| 6,454,795 B1 | | 9/2002 | Chuter |
| 6,458,153 B1 | | 10/2002 | Bailey et al. |
| 6,468,303 B1 | | 10/2002 | Amplatz et al. |
| 6,527,746 B1 | | 3/2003 | Oslund et al. |
| 6,626,936 B2 | | 9/2003 | Stinson |
| 6,641,610 B2 | | 11/2003 | Wolf et al. |
| 6,645,143 B2 | | 11/2003 | Van Tassel et al. |
| 6,666,885 B2 | | 12/2003 | Moe |
| 6,712,836 B1 | | 3/2004 | Berg et al. |
| 6,837,901 B2 | | 1/2005 | Rabkin et al. |
| 6,866,679 B2 | | 3/2005 | Kusleika |
| 6,911,037 B2 | | 6/2005 | Gainer et al. |
| 6,913,614 B2 | | 7/2005 | Marino et al. |
| 6,936,058 B2 | | 8/2005 | Forde et al. |
| 6,979,343 B2 | | 12/2005 | Russo et al. |
| 7,001,409 B2 | | 2/2006 | Amplatz et al. |
| 7,097,653 B2 | | 8/2006 | Freudenthal et al. |
| 7,105,024 B2 | | 9/2006 | Richelsoph |
| 7,159,593 B2 | | 1/2007 | McCarthy et al. |
| 7,226,466 B2 | | 6/2007 | Opalski |
| 7,317,951 B2 | | 1/2008 | Schneider et al. |
| 7,338,514 B2 | | 3/2008 | Wahr et al. |
| 7,419,498 B2 | | 9/2008 | Opalski et al. |
| 7,445,630 B2 | | 11/2008 | Lashinski et al. |
| 7,473,266 B2 | | 1/2009 | Glaser |
| 7,485,141 B2 | | 2/2009 | Majercak et al. |
| 7,524,330 B2 | | 4/2009 | Berreklouw |
| 7,530,995 B2 | | 5/2009 | Quijano et al. |
| 7,625,392 B2 | | 12/2009 | Coleman et al. |
| 7,658,747 B2 | | 2/2010 | Forde et al. |
| 7,699,297 B2 | | 4/2010 | Cicenas et al. |
| 7,766,966 B2 | | 8/2010 | Richelsoph |
| 7,819,890 B2 | | 10/2010 | Russo et al. |
| 7,842,026 B2 | | 11/2010 | Cahill et al. |
| 7,871,419 B2 | | 1/2011 | Devellian et al. |
| 7,927,370 B2 | | 4/2011 | Webler et al. |
| 7,976,564 B2 | | 7/2011 | Blaeser et al. |
| 8,034,061 B2 | | 10/2011 | Amplatz et al. |
| 8,043,360 B2 | | 10/2011 | McNamara et al. |
| 8,048,147 B2 | | 11/2011 | Adams |
| 8,070,708 B2 | | 12/2011 | Rottenberg et al. |
| 8,091,556 B2 | | 1/2012 | Keren et al. |
| 8,157,860 B2 | | 4/2012 | McNamara et al. |
| 8,172,896 B2 | | 5/2012 | McNamara et al. |
| 8,252,042 B2 | | 8/2012 | McNamara et al. |
| 8,460,372 B2 | | 6/2013 | McNamara et al. |
| 2001/0029368 A1 | | 10/2001 | Berube |
| 2002/0029061 A1 | | 3/2002 | Amplatz et al. |
| 2002/0062135 A1 | | 5/2002 | Mazzocchi et al. |
| 2002/0072765 A1 | | 6/2002 | Mazzocchi et al. |
| 2002/0077698 A1 | | 6/2002 | Peredo |
| 2002/0082525 A1 | | 6/2002 | Oslund et al. |
| 2002/0082613 A1 | | 6/2002 | Hathaway et al. |
| 2002/0095172 A1 | | 7/2002 | Mazzocchi et al. |
| 2002/0095173 A1 | | 7/2002 | Mazzocchi et al. |
| 2002/0120277 A1 | * | 8/2002 | Hauschild ............ A61B 17/221 606/108 |
| 2002/0143289 A1 | | 10/2002 | Ellis et al. |
| 2002/0161424 A1 | | 10/2002 | Rapacki et al. |
| 2002/0161432 A1 | | 10/2002 | Mazzucco et al. |
| 2002/0165606 A1 | | 11/2002 | Wolf et al. |
| 2002/0169377 A1 | | 11/2002 | Khairkhahan et al. |
| 2002/0173742 A1 | | 11/2002 | Keren et al. |
| 2002/0177894 A1 | | 11/2002 | Acosta et al. |
| 2002/0183826 A1 | | 12/2002 | Dorn et al. |
| 2002/0198563 A1 | | 12/2002 | Gainor et al. |
| 2004/0044351 A1 | | 3/2004 | Searle |
| 2004/0087937 A1 | | 5/2004 | Eggers et al. |
| 2004/0093075 A1 | | 5/2004 | Kuehne |
| 2004/0102719 A1 | | 5/2004 | Keith et al. |
| 2004/0111095 A1 | | 6/2004 | Gordon et al. |
| 2004/0133236 A1 | | 7/2004 | Chanduszko et al. |
| 2004/0143292 A1 | | 7/2004 | Marino |
| 2004/0162514 A1 | | 8/2004 | Alferness et al. |
| 2004/0176788 A1 | | 9/2004 | Opolski |
| 2004/0193261 A1 | | 9/2004 | Berreklouw |
| 2004/0206363 A1 | | 10/2004 | McCarthy et al. |
| 2002/0220653 | | 11/2004 | Borg et al. |
| 2004/0236308 A1 | | 11/2004 | Herweck et al. |
| 2004/0243143 A1 | | 12/2004 | Corcoran et al. |
| 2004/0267306 A1 | | 12/2004 | Blaeser et al. |
| 2005/0049692 A1 | | 3/2005 | Numamoto et al. |
| 2005/0065548 A1 | | 3/2005 | Marino et al. |
| 2005/0065589 A1 | | 3/2005 | Schneider et al. |
| 2005/0070934 A1 | | 3/2005 | Tanaka et al. |
| 2005/0075655 A1 | | 4/2005 | Bumbalough et al. |
| 2005/0080400 A1 | | 4/2005 | Corcoran et al. |
| 2005/0148925 A1 | | 7/2005 | Rottenberg et al. |
| 2005/0165344 A1 | | 7/2005 | Dobak |
| 2005/0187616 A1 | | 8/2005 | Realyvasquez |
| 2005/0222604 A1 | * | 10/2005 | Schaeffer .................. A61F 2/01 606/200 |
| 2005/0240205 A1 | | 10/2005 | Berg et al. |
| 2005/0267523 A1 | | 12/2005 | Devellian et al. |
| 2005/0273075 A1 | | 12/2005 | Krulevitch et al. |
| 2005/0288722 A1 | | 12/2005 | Eigler et al. |
| 2006/0004434 A1 | | 1/2006 | Forde et al. |
| 2006/0009715 A1 | | 1/2006 | Khairkhahan et al. |
| 2006/0009800 A1 | | 1/2006 | Christianson et al. |
| 2006/0122646 A1 | | 6/2006 | Corcoran et al. |
| 2006/0122647 A1 | | 6/2006 | Callaghan et al. |
| 2006/0136043 A1 | | 6/2006 | Cully et al. |
| 2006/0155305 A1 | | 7/2006 | Freudenthal et al. |

(56) References Cited

U.S. PATENT DOCUMENTS

| | | |
|---|---|---|
| 2006/0184088 A1 | 8/2006 | Van Bibber et al. |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0276882 A1 | 12/2006 | Case et al. |
| 2007/0016250 A1 | 1/2007 | Blaeser et al. |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0168019 A1 | 7/2007 | Amplatz et al. |
| 2007/0185513 A1 | 8/2007 | Woolfson et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rattenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |
| 2008/0125861 A1 | 5/2008 | Webler et al. |
| 2008/0154302 A1 | 6/2008 | Opolski et al. |
| 2008/0154351 A1 | 6/2008 | Leewood et al. |
| 2008/0172123 A1 | 7/2008 | Yadin |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0221582 A1* | 9/2008 | Gia ............... A61B 17/221 606/99 |
| 2008/0228264 A1 | 9/2008 | Li et al. |
| 2008/0249612 A1 | 10/2008 | Osborne et al. |
| 2008/0262592 A1 | 10/2008 | Jordan et al. |
| 2008/0312679 A1 | 12/2008 | Hardert et al. |
| 2009/0018562 A1 | 1/2009 | Amplatz et al. |
| 2009/0025820 A1 | 1/2009 | Adams |
| 2009/0030495 A1 | 1/2009 | Koch |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal et al. |
| 2009/0131978 A1 | 5/2009 | Gainor et al. |
| 2009/0171386 A1 | 7/2009 | Amplatz et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030321 A1 | 2/2010 | Mach |
| 2010/0049307 A1 | 2/2010 | Ren |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Devellian et al. |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg |
| 2011/0257723 A1 | 10/2011 | McNamara et al. |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2012/0053686 A1 | 3/2012 | McNamara et al. |
| 2012/0130301 A1 | 5/2012 | McNamara et al. |
| 2012/0165928 A1 | 6/2012 | Nitzan et al. |
| 2012/0259263 A1 | 10/2012 | Celermajer et al. |
| 2012/0265296 A1 | 10/2012 | McNamara et al. |
| 2012/0289882 A1 | 11/2012 | McNamara et al. |
| 2012/0289971 A1* | 11/2012 | Segermark ........... A61B 17/221 606/108 |
| 2012/0290062 A1 | 11/2012 | McNamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0204175 A1 | 8/2013 | Sugimoto |
| 2013/0231737 A1 | 9/2013 | McNamara et al. |
| 2013/0267885 A1 | 10/2013 | Celermajer et al. |

FOREIGN PATENT DOCUMENTS

| | | |
|---|---|---|
| WO | 199527448 | 10/1995 |
| WO | 2008058940 | 5/2008 |
| WO | 2010111666 | 9/2010 |
| WO | 2014150106 | 9/2013 |

OTHER PUBLICATIONS

Althoff et al., "Long-Term Follow up of a Fenestrated Amplatzer Atrial Septal Occluder in Pulmonary Arterial Hypertension," Chest 2008, 133:183-85, 5 pages.

Atz et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, pp. 1224-1228.

Bailey, "Nanotechnology in Prosthetic Heart Valves," date 2005, presentation, 31 pages.

Bolling, "Direct Flow Medical—My Valve is Better." Apr. 23, 2009, presentation, 21 pages.

Cheatham, John P., "Intervention in the critically ill neonate and infant with hypoplastic left heart syndrome and intact atrial septum", Journal of Interventional Cardiology, vol. 14, No. 3, 2001, pp. 357-366.

Coselli, Joseph S., "Not valve replacement: patientcu prosthetic mismatch rarely occurs," Texas Heart Insitute, Apr. 2009, 75 pages.

Design News, "Low Power Piezo Motion", http://www.designnews. com/document.asp?doc—id=229053&dfpPParams&dfpPParams= ht—13,aid—229053&dfpLayout=article, May 14, 2010, 3 pages.

(56) References Cited

OTHER PUBLICATIONS

European Application Serial No. EP10772411.4, European Search Opinion and Supplementary European Search Report dated Mar. 16, 2012, 5 pages.
European Application Serial No. EP12180631.9, European Search Report dated Nov. 19, 2012, 5 pages.
Gaudiani et al., "A Philosophical Approach to Mitral Valve Repair," Apr. 24, 2009, presentation, 28 pages.
Hijazi, "Valve Implantation, Ziyad M. Hijazi," May 10, 2007, presentation, 36 pages.
International Application Serial No. PCT/AU2007/001704, International Preliminary Report on Patentability, dated Aug. 22, 2008, 5 pages.
International Application Serial No. PCT/AU2007/001704, International Search Report, dated Jan. 16, 2008, 4 pages.
International Application Serial No. PCT/AU2007/001704, Written Opinion, dated Jan. 16, 2008, 5 pages.
International Application Serial No. PCT/US2010/026574, International Preliminary Report on Patentability, dated Nov. 10, 2011, 6 pages.
International Application Serial No. PCT/US2010/026574, International Search Report, dated Nov. 19, 2010, 5 pages.
International Application Serial No. PCT/US2010/058110, International Preliminary Report on Patentability, dated Nov. 27, 2012, 7 pages.
International Application Serial No. PCT/US2010/058110, International Search Report and Written Opinion, dated Aug. 26, 2011, 12 pages.
International Application Serial No. PCT/US2011/022895, International Search Report & Written Opinion, dated Oct. 24, 2011, 10 pages.
International Application Serial No. PCT/US2011/041841, International Preliminary Report on Patentability and Written Opinion, dated Jun. 6, 2013, 7 pages.
International Application Serial No. PCT/US2011/041841, International Search Report and Written Opinion, dated Feb. 9, 2012, 10 pages.
International Application Serial No. PCT/US2012/024680, International Preliminary Report on Patentability and Written Opinion, dated Aug. 22, 2013, 6 pages.
International Application Serial No. PCT/US2012/024680, International Search Report and Written Opinion, dated Oct. 23, 2012, 10 pages.
International Application Serial No. PCT/US2012/071588, International Search Report and Written Opinion, dated Apr. 19, 2013, DC Devices, Inc., 17 pages.
Larios et al., "The Use of an Artificial Foraminal Valve Prosthesis in the Closure of Interatrial and Interventricular Septal Defects," Dis. Chest. 1959: 36; 631-41, 11 pages.
Leon, "Transcatheter Aortic Valve Therapy: Summary Thoughts," Jun. 24, 2009, presentation, 19 pages.
Merchant et al., "Advances in Arrhythmia and Electrophysiology; Implantable Sensors for Heart Failure", Circ. Arrhythm. Electrophysiol., vol. 3, Dec. 2010, pp. 657-667.
Moses, "The Good, the Bad and the Ugly of Transcatheter AVR," Jul. 10, 2009, presentation, 28 pages.
O'Loughlin et al., "Insertion of a Fenestrated Amplatzer Atrial Sestosotomy Device for Severe Pulmonary Hypertension," Heart Lung Circ. 2006, 15(4):275-77, 3 pages.
Park et al., "Blade atrial septostomy: collaborative study", Circulation, Journal of the American Heart Association, vol. 66, No. 2, Aug. 1982, pp. 258-266.
Pedra et al., "Stent Implantation to Create Interatrial Communications in Patients With Complex Congenital Heart Disease", Catheterization and Cardiovascular Interventions 47, Jan. 27, 1999, pp. 310-313.
Perry et al., "Creation and Maintenance of an Adequate Interatrial Communicationin left Atrioventricular Valve Atresia or Stenosis", The American Journal of Cardiology, vol. 58, Sep. 15, 1986, pp. 622-626.
Philips et al., "Ventriculofemoroatrial shunt: a viable alternative for the treatment of hydrocephalus", J. Neurosurg., vol. 86, Jun. 1997, pp. 1063-1066.
Sommer et al., "Transcatheter Creation of Atrial Septal Defect and Fontan Fenestration with "Butterfly" Stent Technique", Supplement to Journal of the American College of Cardiology, vol. 33, No. 2, Supplement A, Feb. 1999, 3 pages.
Stone, "Transcatheter Devices for Mitral Valve Repair, Surveying the Landscape," Jul. 10, 2009, presentation, 48 pages.
Stormer et al., "Comparative Study of in vitro Flow Characteristics between a Human Aortic Valve and a Designed Aortic Valve and Six Corresponding Types of Prosthetic Heart Valves," Eur. Surg. Res. 8: 117-131 (1976), 15 pages.
Watterson et al., "Very Small Pulmonary Arteries: Central End-to-Side Shunt", Ann. Thorac. Surg., vol. 52, No. 5, Nov. 1991, pp. 1132-1137.

* cited by examiner

IMPLANT RETENTION ATTACHMENT AND METHOD OF USE

CROSS-REFERENCES TO RELATED APPLICATIONS

This application claims priority to and benefit of U.S. Provisional Application No. 61/635,842, filed Apr. 19, 2012, the contents of which are incorporated by reference herein in its entirety.

FIELD

The present teachings relate generally to percutaneous delivery systems and methods of use thereof to deliver a cardiac implant. An example of the present teachings relates to an implant retention mechanism in the delivery system that allows a clinician to assess the deployment of the implant, while maintaining contact with the implant. Such implant retention mechanism allows a clinician to retrieve a deployed implant either by using a separate implant retrieval mechanism or by using the implant retention mechanism. The present teachings further relate to a method of utilizing such percutaneous delivery systems, for example, in treating congestive heart failure or other diseases.

BACKGROUND

In a healthy heart, blood that returns from the body to the right atrium is low in oxygen. This blood passes through the right ventricle to the lungs to be enriched with oxygen. The oxygen-rich blood returns to the left atrium, and then to the left ventricle. It is then pumped out to the body through the aorta, a large blood vessel that carries the blood to smaller blood vessels in the body. The right atrium and the left atrium are separated by a thin wall, called the atrial septum.

An atrial septal defect (ASD), i.e., a hole in the atrial septum, is a congenital heart defect. A patent foramen ovale (PFO) is also a congenital heart defect in the septum between the two atria of the heart. In PFO, the defect is a flap or a valve-like opening in the atrial septal wall.

The presence of a large ASD or PFO may result in a left-to-right shunt, which allows blood to flow from the left atrium to the right atrium. This extra blood from the left atrium may cause a volume overload in both the right atrium and the right ventricle. Left untreated, this condition can result in enlargement of the right side of the heart and ultimately heart failure.

Congestive heart failure (CHF) is a condition afflicting millions of people worldwide. CHF resulting from a weakening or stiffening of the heart muscle most commonly is caused by myocardial ischemia (due to, e.g., myocardial infarction) or cardiomyopathy (e.g., myocarditis, amyloidosis). CHF causes a reduced cardiac output and inadequate blood to meet the needs of the body.

CHF is generally classified into systolic heart failure (SHF) or diastolic heart failure (DHF). In SHF, the pumping action of a heart is reduced or weakened. A normal ejection fraction (EF), which is a function of the volume of blood ejected out of the left ventricle (stroke volume) divided by the maximum volume remaining in the left ventricle at the end of the diastole or relaxation phase, is greater than 50%. In a systolic heart failure, the EF is decreased to less than 50%. A patient with SHF may have an enlarged left ventricle because of cardiac remodeling developed to maintain an adequate stroke-volume. This pathophysiological phenomenon is often associated with increased atrial pressure and left ventricular filling pressure.

DHF is a heart failure often without any major valve disease or any impediment to the systolic function of the left ventricle. Generally, DHF is the failure of the ventricle to adequately relax and expand, resulting in a decrease in the stroke volume of the heart. There are very few treatment options for patients suffering from DHF. DHF afflicts between 30% and 70% of CHF patients.

Cardiac implants in the atrial septum have been used for many purposes. For example, septal occluders can be used for transcatheter closure of congenital heart defects, such as the atrial septal defects or the patent foramen ovale; and atrial shunt devices can be used to treat congestive heart failures by allowing a small volume of blood to travel from the left side of the heart to the right side of the heart, thereby reducing the left atrial pressure.

Most percutaneous deployment of a cardiac implant in the atrial septum is conducted through a standard right heart catheterization procedure. In such a procedure, a cardiac implant is delivered through the femoral vein, to the inferior vena cava and, to the right atrium. As shown in FIG. 1, as a delivery system enters the right atrium, it extends toward the atrial septum in an acute angle "θ". Most cardiac implants, as being deployed from the delivery system, are generally at a right angle to the longitudinal axis of the delivery system. Thus, when the implant is being deployed at the atrial septum but before released from the delivery system, the implant deployment position can be distorted by the strain imposed by the delivery system to the atrial septum. In such an event, when a clinician releases the implant, and as the distorted septum resumes its natural state, the implant deployment position can change in the process. In certain instances, the released implant can be improperly deployed and must be retrieved to prevent embolization. Thus, there is a need for a clinician to assess the "true" deployment status of the cardiac implant, i.e., how the implant is positioned in its released state, while still maintaining contact with the implant. In the event that the implant is not successfully deployed, the clinician can recapture the implant by using the implant retention mechanism or an implant retrieval mechanism.

SUMMARY

An aspect of the present teachings provides a delivery system having an implant retention mechanism. In various embodiments, the implant retention mechanism allows a clinician to assess a deployed implant that is free from any distortion or under a reduced distortion caused by the strain imposed upon the delivery system by the atrial septum at an acute angle. Another aspect of the present teachings is to provide a delivery system with an implant retention mechanism for delivering, for example, percutaneously, a cardiac implant. In various embodiments, the delivery system includes a delivery sheath, a delivery catheter, and an implant retention mechanism.

According to various embodiments of the present teachings, the delivery system includes a relatively flexible implant retention mechanism that retains an implant during its deployment. In various embodiments, the relatively flexible implant retention mechanism includes an implant retention string with a fixed end and a free end. In some embodiments of the present teachings, the fixed end of the retention string connects to a portion of the delivery catheter. In some embodiments, the free end of the string extends from its fixed end, crosses a retention outlet on the implant device, extends proximally through a lumen of the delivery sheath, and exits the proximal end of the delivery sheath.

In various embodiments of the present teachings, the fixed end of the implant retention string attaches to the delivery catheter by wrapping at least partially circumferentially around a portion of the delivery catheter in one or more loops and is trapped by the delivery sheath during the implant deployment. In various other embodiments of the present teachings, during an implant deployment, the delivery sheath is pulled proximally, exposing the wrapped loop of the fixed end of the retention string, allowing the loop to unravel itself, thereby releasing its attachment to the delivery catheter.

According to various embodiments of the present teachings, the flexible retention string is tied to the implant through the implant retention outlet, forming an exploding knot. In various embodiments of the present teachings, both ends of the knot extend proximally through the lumen of the delivery sheath. During delivery and deployment of an implant, a first end of the flexible retention string is held so that the implant remains in contact with the delivery system. During the implant release, a second end of the flexible retention string is pulled, allowing the exploding knot to untie itself, thereby releasing the implant from the delivery system.

According to various embodiments of the present teachings, the delivery system includes a relatively rigid implant retention mechanism. In various embodiments of the present teachings, such a relatively rigid implant retention mechanism includes an implant retention wire with a fixed end attached to a portion of the delivery catheter and a free end extending from its fixed end, passing through a retention outlet on the implant device, extending proximally through a lumen of the delivery sheath, and releasably secured on the delivery system. During the delivery of an implant, the free end of the retention wire extends from its fixed end, crosses the implant retention outlet, and is releasably secured on the delivery system. During the release of the implant, the free end of the retention wire is released from its attachment to the delivery system, thereby releasing the implant.

According to yet another embodiment of the present teachings, the retention wire has elasticity or a shape memory, allowing the free end of the retention wire to be constrained by the delivery system, and allowing the retention wire to resume a relatively straight profile after its free end is released from the delivery system. According to another embodiment of the present teachings, the releasable securing of the free end of the retention wire is achieved by a dimensional interference.

According to various embodiments of the present teachings, the delivery system includes a delivery sheath, a delivery catheter, and an implant retention mechanism. In some embodiments, the implant retention mechanism includes an elongated tube, an implant retention mandrel, and an implant retention wire. According to certain embodiments of the present teachings, the elongated implant retention mandrel is slidably disposed within the elongated tube. In certain embodiments, the implant retention wire has a fixed end connected to a portion of the implant retention mandrel and a free end releasably secured on the implant retention mechanism.

In various embodiments of the present teachings, the implant retention mechanism includes an implant retention wire with a proximal end, a free end, and an elongated body extending between the proximal end and the free end. According to various embodiments of the present teachings, the implant retention wire is slidably disposed within a longitudinal lumen of the delivery catheter. During an implant delivery and deployment, the free end of the retention wire extends distally, crosses the implant retention outlet, turns and extends proximally. During the implant release, the implant retention wire extends distally until its free end extends beyond the distal end of the delivery system, thereby releasing the implant.

According to various embodiments of the present teachings, the implant retention mechanism includes a delivery catheter and a retention wire having a proximal end and a distal bend and a retention wire cavity on a distal end portion of the delivery catheter. The distal bend of the retention wire extends radially toward the longitudinal axis of the delivery system. According to various embodiments of the present teachings, the implant retention wire has a "stowed" configuration and a radially expanded configuration. In its stowed configuration, the delivery sheath slides over the implant retention wire with the distal bend of the retention wire remaining inside the wire retention cavity, thereby retaining the implant. In its radially expanded configuration, the distal bend of the retention wire expands radially outward and releases the end of the distal bend of the retention wire from the wire retention cavity, thereby releasing the implant.

According to various embodiments of the present teachings, the implant retention mechanism includes a delivery catheter and a retention wire having a proximal end and a distal end and a retention wire cavity on a distal end portion of the delivery catheter. During the delivery of an implant, the retention wire extends through the implant retention outlet so that the distal end of the retention wire is positioned within the wire retention cavity on the delivery catheter.

According to various embodiments of the present teachings, the implant retention mechanism includes a wire retention cavity and an implant retention wire having a locked configuration and an unlocked configuration. In its unlocked configuration, the distal portion of the retention wire releases the distal end of the retention wire from the wire retention cavity, thereby releasing the implant. In its locked configuration, the distal end of the retention wire remains inside the wire retention cavity and retains the implant.

According to various embodiments of the present teachings, the implant retention mechanism includes an elongated retention wire tube and a retention wire slidably disposed within the elongated retention wire tube. In some embodiments of the present teachings, the retention wire tube has a side open near its distal end on its tubular surface.

According to various embodiments of the present teachings, the implant retention mechanism comprises an elongated lumen and an implant retention wire having a locked configuration and an unlocked configuration. In its unlocked configuration, the distal end of the retention wire releases the distal end of the retention wire from the elongated lumen of the retention distal to a side opening, and extends outside of the side opening of the tube, thereby releasing the implant. In its locked configuration, the distal end of the retention wire remains inside the elongated lumen of the retention distal to the side opening of the tube and retains the implant.

According to various embodiments of the present teachings, a delivery system includes a delivery sheath, a delivery catheter and at least one implant retention wire. In some embodiments, the delivery sheath has a proximal end, a distal end, and an elongated lumen extending from its proximal end to the distal end and the delivery catheter is slidably disposed within the delivery sheath. In certain embodiments, the delivery catheter also has a proximal end, a distal end, and at least one elongated lumen extending from the proximal end to the distal end and the at least one implant retention wire slidably disposed within the at least one elongated lumen. In certain embodiments, the delivery catheter also includes at least one surface cavity deep enough to intersect with the elongated lumen.

In various embodiments of the present teachings, during an implant delivery and deployment, the proximal end of the implant folds radially inwardly and is disposed within a surface cavity of the delivery catheter. In addition, the exemplary implant can have an implant retention outlet located on the folded proximal end portion of the implant. In some embodiments, the delivery catheter includes an implant retention wire extending within the elongated lumen of the delivery catheter, through the surface cavity of the delivery catheter, through the implant retention outlet, and extending further into the distal end of the lumen.

According to various embodiments of the present teachings, the implant retention wire has a locked configuration and an unlocked configuration. In its locked configuration, the distal portion of the retention wire extends through the surface cavity intersecting the elongated lumen, extends through the implant retention outlet folded within, and retains the implant. In its unlocked configuration, the distal portion of the retention wire retracts from the surface cavity intersecting the elongated lumen, thereby releasing the implant.

DETAILED DESCRIPTION

The present teachings provide a delivery system comprising an implant retention mechanism for delivering a cardiac implant. In various embodiments, the implant retention mechanism allows a clinician assesses an implant deployment with the implant free from strain imposed by the delivery system to the atrial septum. The present teachings can be incorporated into delivery systems for many atrial implants, such as ASD closure devices, PFO closure implants, atria shunting devices, etc. A delivery system generally can include a delivery sheath, a delivery catheter, and an implant retention mechanism. In some embodiments, the delivery sheath has a proximal end, a distal end, a longitudinal axis, and a longitudinal lumen extending from the proximal end to the distal end. In some embodiments, the delivery catheter also has a proximal end, a distal end, and a longitudinal axis. In some embodiments, the delivery catheter also has a longitudinal lumen extending from the proximal end to the distal end. In one embodiment, during a percutaneous delivery process, an implant can be folded into an elongated delivery configuration and stowed inside the longitudinal lumen of the delivery sheath. In another embodiment, the distal end of the delivery catheter is in contact with the proximal end of the implant during the delivery. In one embodiment, the implant, in an elongated delivery configuration, slides over a distal end portion of the delivery catheter during the delivery. In another embodiment, during a percutaneous delivery process, an implant can be folded into an elongated delivery configuration and stowed inside the longitudinal lumen of the delivery catheter.

As used herein, the term "proximal" shall mean closest to the operator (less into the body) and "distal" shall mean furthest from the operator (further into the body). In positioning the medical device from a downstream access point, distal is more upstream and proximal is more downstream.

Additionally, the term "delivery configuration" used herein refers to the configuration of a device, such as an occluder, when it has a reduced profile in a delivery catheter. The term "deployed configuration" refers to the configuration of a device, such as an occluder, when it is deployed from the catheter, such as at the desired implantation location.

The present teachings can be more fully described hereinafter with reference to the accompanying drawings, which show certain preferred embodiments of the present teachings. The present teachings may, however, be embodied in many different forms and should not be construed as being limited to the embodiments set forth herein; rather, these embodiments are provided to illustrate various aspects of the present teachings. Like numbers refer to like elements throughout.

Figure 1:
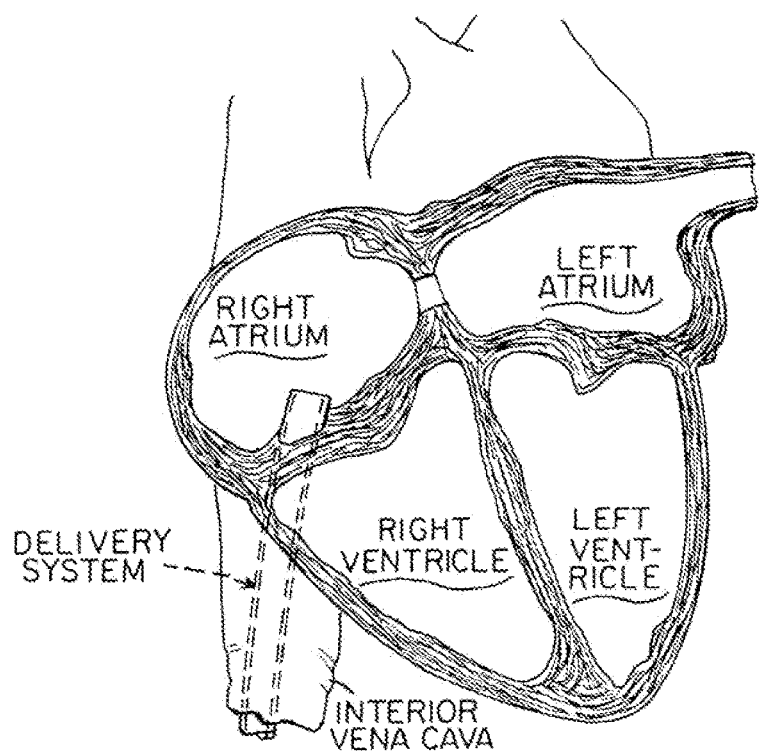
FIG. 1 is a perspective view of an exemplary medical device delivery system entering the right atrium of a heart in accordance with the present teachings.
Figure 2:
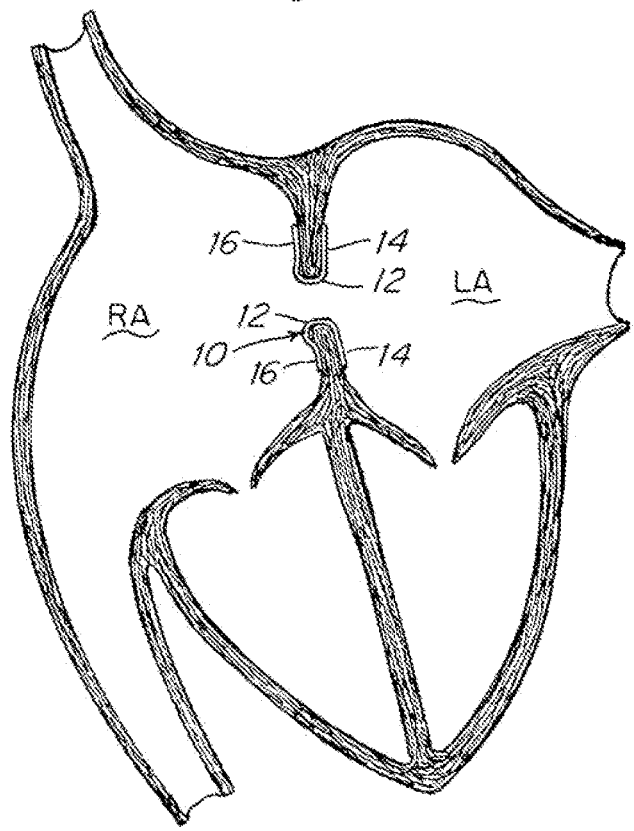
FIG. 2 is a perspective view of the exemplary medical device deployed at a target site between the left and right atrium of a heart in a constrained configuration.

For the sole purpose of illustrating how certain embodiments of the present teachings function, an example of a cardiac implant is used herewith. FIG. 2 illustrates one such example, where a cardiac implant (10) is positioned through an aperture between the left and right atria. As used herein, unless otherwise indicated, the term "aperture" refers to any anatomical anomalies such as a PFO, an ASD, a VSD, or an anatomical feature created for the purpose of creating a shunt. As shown in FIG. 2, an exemplary implant device includes a body portion (12), at least one distal flanges (14), and at least one proximal flanges (16) connecting to the body portion (12) at its distal end and the proximal end respectively. Upon deployment, as seen in FIG. 2, the body portion (12) of the implant device is positioned through the aperture of the atrial septum, the distal flanges (14) of the device are positioned inside the left atrium contacting the septum, and the proximal flanges (16) of the device are positioned inside the right atrium contacting the septum. In this exemplary embodiment, the distal flanges (14) and the proximal flanges (16) are substantially annular and extend radially outward from the longitudinal axis of the body portion (12) as seen in FIG. 2. According to various embodiments of the present teachings, the implant device has an elongated profile for percutaneous delivery through a delivery system and resumes a radially expanded profile upon deployment, as described in FIG. 2.

The examples of the cardiac implant described in conjunction with the drawings of the present application have some similarities to those in U.S. Pat. No. 8,043,360, filed on Mar. 8, 2010; U.S. patent application Ser. No. 12/719,834, filed on Mar. 8, 2010; U.S. patent application Ser. No. 12/719,840, filed on Mar. 8, 2010; U.S. patent application Ser. No. 12/719,843, filed on Mar. 8, 2010; and U.S. patent application Ser. No. 12/848,084, filed on Jul. 30, 2010; each of which is incorporated by reference herein in its entirety. It, however, should be understood by those skilled in the art that other cardiac implants can also be used with embodiments of the present teachings presented herein, such as atrial septal defect occluders, PFO occluders and the like.

Figure 3:
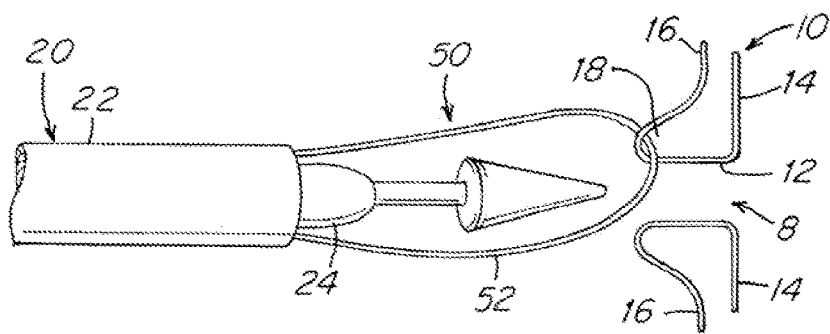
FIG. 3 is a perspective view of an exemplary medical device delivery system attaching to a deployed medical device according to the present teachings.

Referring now to FIG. 3, as implant been deployed at atrial septum (not shown), the implant expands radially with its body portion (12) positioned through an aperture on the atrial septum, distal flange (14) apposed against the atrial septum in the left atrium, and proximal flange (16) apposed against the atrial septum in the right atrium. According to the embodiment of the present teachings, the implant deployment is accomplished by either retracting the delivery sheath (22) proximally, or by extending the delivery catheter (24) distally, or a combination of both, thereby allowing the implant (10) exit the distal end of the delivery sheath, and resume its radially expanded profile. The techniques disclosed for deploying a cardiac implant described herein are only examples of deployment technique. It should be understood that other techniques can be used instead of, or in combination with, those disclosure. For example, the techniques used to deploy an embodiment of the cardiac implant described herein will depend on the particular features of the device, the delivery system, and the anatomy in which the device is being deployed.

Although details vary from one embodiment to another embodiment, according to various embodiments of the present teachings, the implant device includes at least one retention outlet working together with an implant retention mechanism. In some embodiments of the present teachings, the retention outlet is on the proximal flanges of the cardiac implant. In an alternative embodiment, the retention outlet is on the body portion of the cardiac implant. According to another embodiment of the present teachings, the retention outlet is on the distal portion of the cardiac implant. An implant retention outlet is a hollow place in a solid body or surface of the implant which allows a wire or a filament to pass through one side of the outlet to the other side. According to various embodiments of the present teachings, an implant retention outlet is a close loop, where an implant retention mechanism extends from one side of the solid body or surface of the cardiac implant to another, and can only be released by reversal of this movement.

The present teachings provide a delivery system with an implant retention mechanism for percutaneous delivery of cardiac implants. In various embodiments, the implant retention mechanism retains a deployed implant by engaging its implant retention outlet. In some embodiments, a relatively flexible implant retention mechanism is used for implant retention. In other embodiments, a relatively rigid implant retention mechanism is used for implant retention. Examples of these embodiments are described in detail below.

Flexible Retention Mechanism

In various embodiments, a relatively flexible implant retention mechanism retains an implant during its deployment process, imposing minimum or no strain to the movement of the implant. By using these embodiments, a clinician can assess the true deployment status with confidence that the deployment position will not change during or after the releasing process of the implant. According to some embodiments, the implant retention mechanism includes a retention string that is not only strong enough to hold the implant securely, but also flexibly enough to allow the implant to be positioned naturally in the atrial septum and conform to the dynamic environment of a beating heart.

According to various embodiments of the invention, the flexible implant retention mechanism is also strong enough to be used to retrieve a deployed implant by pulling the implant proximally back into its delivery catheter/sheath or a retrieval catheter/sheath. Alternatively, the flexible implant retention mechanism can be used to guide implant retrieval by allowing an implant retrieval system to slide over the implant retention mechanism and locate/reach the implant.

As described in detail below, a flexible implant retention mechanism can include an implant retention string. While the description above refers to strings, other terms, for example, filaments or sutures, are essentially interchangeable. One skilled in the art will also understand that certain metallic wires can also be used as the retention string, such as stainless steel wire, nitinol wire, etc. In addition, in some embodiments, each string, suture, or filament comprises one or more strings, sutures, or filaments.

According to various embodiments, the implant retention string could be made from numerous materials, either polymeric or metallic. The polymeric retention string material can be polyglycolic acid (Biovek), polylactic acid, polydioxanone, and caprolactone, synthetics polypropylene, polyester or nylon etc. In another embodiments, other non-absorbable retention string material, for example, special silk, can be used.

In one embodiment of the present teachings, the cross section of the implant retention string may be circular or polygonal, such as square, or hexagonal. In another embodiment of the present teachings, the cross section of the implant retention string has a general diameter of 0.01 mm to 2 mm. In one embodiment of the present teachings, the implant retention string has a consistent cross section shape and size throughout its entire length. In another embodiment of the present teachings, the implant retention string has various shaped and sized cross section throughout its entire length. In one embodiment of the present teachings, the implant retention string has a length one to more than two times of the length of the delivery system.

Referring to one preferred embodiment, as illustrated in FIG. 3, a delivery system (20) with a flexible implant retention mechanism (50) is used for delivering a cardiac implant (10). FIG. 3 illustrates a cardiac implant (10) deployed in the heart (not shown) with an exemplary flexible implant retention mechanism (50) still engaging the implant (10). In this embodiment, the delivery system (20) includes a delivery sheath (22), which includes a distal end, a proximal end, and a longitudinal lumen extending, along a longitudinal axis, from the proximal end to the distal end; a delivery catheter (24), which includes a proximal end and a distal end and is slidably disposed within the longitudinal lumen of the delivery sheath (22); and a flexible implant retention mechanism (50), which includes, among others, an implant retention string (52) with a fixed end (54) and a free end (56).

Referring to FIG. 3, the exemplary implant retention mechanism (50) includes a retention string (52) with a fixed end (54) (not shown) and a free end (56) (not shown). The fixed end of the retention string is connected to a distal end portion of the delivery catheter (24). The free end (56) of the retention string extends from the distal end portion of the delivery catheter (24), crosses the retention outlet (18) on the implant (10), extends proximally through the lumen of the delivery sheath (22), and exits the proximal end of the delivery sheath (22).

In this exemplary embodiment, the implant (10) has a longitudinal lumen (8) extending from one end of the body portion (12) to the other end of the body portion (12), so that the body portion (12) of the implant (10) has an outer surface which faces, and contacts, the septum at atrial aperture, and an inner surface which faces the longitudinal lumen (8). In one embodiment of the present teachings, the implant retention outlet (18) is located on the body portion (12) of the implant (10). According to one embodiment of the present teachings, the free end (56) (not shown) of the flexible retention string (52) extends along the outer surface of the body portion (10); crosses the implant retention outlet (18); extends proximally along the inner surface of the body portion (10), through the longitudinal lumen (8) of the body portion (12) of the implant (10), and further proximally through the longitudinal lumen of the delivery sheath (22); and exits the proximal end of the delivery sheath (22). In an alternative embodiment, the free end (56) of the flexible retention string (52) extends along the longitudinal lumen (8) of the body portion (10) of the implant (10), crosses the implant retention outlet (18), extends proximally along the outer surface of the body portion (12), and further proximally through the lumen of the delivery sheath (22), and exits the proximal end of the delivery sheath (22).

According to another embodiment, the implant retention outlet (18) is located on a proximal flange (16) of the implant (10). For example, as the implant device is stowed in its elongated profile, the proximal flange (16) retracts radially, forming an elongated proximal flange portion (16) with a longitudinal lumen, so that the elongated proximal flange portion (16) of the implant (10) has an outer surface which, when deployed, faces, and contacts, the septum at atrial aperture, and an inner surface which, when deployed, faces the right atrium. In one embodiment, the free end (56) of the flexible retention string (52) extends along the outer surface of the elongated proximal flange portion (16), crosses the implant retention outlet (18), extends proximally along the inner surface of the elongated proximal flange portion (16), further proximally through the lumen of the delivery sheath (22), and exits the proximal end of the delivery sheath (22). According to an alternative embodiment, the free end (56) of the flexible retention string (52) extends along the inner surface of the elongated proximal flange portion (16), crosses the implant retention outlet (18), extends proximally along the outer surface of the elongated proximal flange portion (16), further proximally through the lumen of the delivery sheath (22), and exits the proximal end of the delivery sheath (22).

Referring to FIG. 3, flexibility of the implant retention string (52) allows a clinician to maintain contact with the implant (10), while the implant (10) conforms to the anatomy of the atrial septum. Such embodiment allows a clinician to assess the true status of an implant deployment before releasing the implant. Such embodiment also eliminates the risk of shifting the implant position when the implant is released from the delivery system (20). In the event that an implant deployment is not satisfactory, a clinician can use an implant retrieval mechanism, for example, by sliding it over the retention string (52), to retrieve the implant (10). In another embodiment, a clinician can retrieve the implant (10) by retracting implant retention string (52) proximally, thereby pulling the implant (10) back into a delivery/retrieval sheath from the distal end.

According to one embodiment of the present teachings, during implant delivery and retention, the fixed end of the flexible retention string (52) is connected to the distal end portion of the delivery catheter (24) and the free end of the flexible retention string (52), after crossing the implant retention outlet, extends through the lumen of the delivery sheath (22). Alternatively, the fixed end (54) of the flexible retention string (52) is connected to the distal end portion of the delivery catheter (24) and the free end (56) of the flexible retention string (52), after crossing the implant retention outlet, extends through the lumen of the delivery catheter (24). In another embodiment of the present teachings, the fixed end (54) of the flexible retention string (52) is connected to the distal end portion of the delivery sheath (22) and the free end (56) of the flexible retention string (52), after crossing the implant retention outlet, extends through the lumen of the delivery sheath (22). Alternatively, the fixed end (54) of the flexible retention string (52) is connected to the distal end portion of the delivery sheath (22) and the free end (56) of the flexible retention string (52) after crossing the implant retention outlet, extends through the lumen of the delivery catheter (24). In yet another embodiment of the present teachings, the fixed end (54) of the flexible retention string (52) is connected to the delivery system handle (not shown) and the free end (56) of the flexible retention string (52), after crossing the implant retention outlet, extends through the lumen of the delivery catheter (24) or delivery sheath (22).

Figure 4:
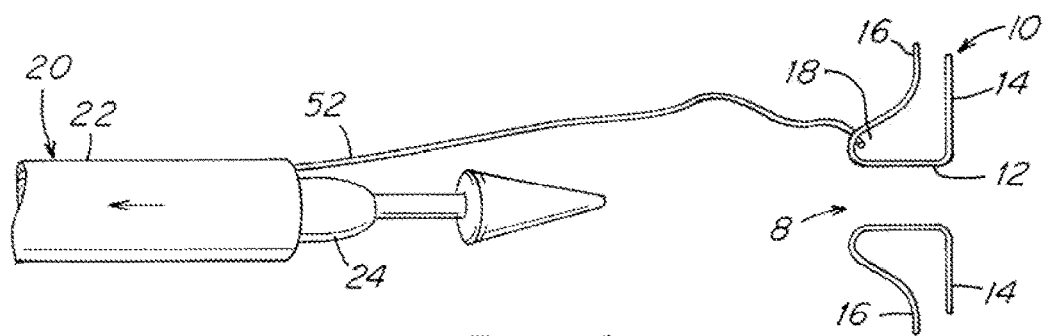
FIG. 4 is a perspective view of an exemplary medical device delivery system of FIG. 3, releasing a deployed medical device according to the present teachings.

In the event that the deployment is successful, as illustrated in FIG. 4, the fixed end of the retention string (54) (not shown) is then retracted proximally by pulling the delivery catheter (24) or delivery sheath (22) proximally, allowing the free end (56) of the flexible retention string (52) to move distally, releasing the string (52) from the implant retention outlet (18), and completely releasing the implant (10).

Figures 5A, 5B, 5C, 5D:
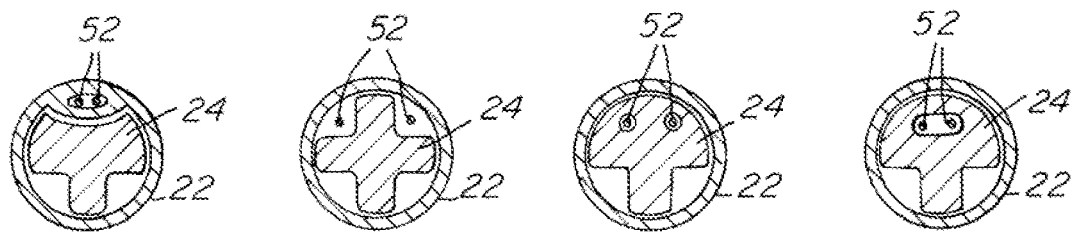
FIGS. 5A-D are cross-sectional profile views of an exemplary medical device delivery system in accordance with the present teachings.

FIGS. 5A-D illustrate cross-section profiles of an exemplary delivery system (20) with a flexible implant retention mechanism (50). In general, the cross-section of the delivery system (20) includes an exemplary cross-section of the delivery sheath (22), an exemplary cross-section of the delivery catheter (24), and an exemplary cross-section of the flexible retention string (52). FIG. 5A illustrates one embodiment of the present teachings, where a lumen is formed in the delivery sheath (22). This lumen is configured to contain a flexible retention string (52), both extending distally from its fixed end (54) to the implant (10), and extending proximally from the implant back to its free end (56). FIG. 5B illustrates that two separate lumens are formed by the outer surface of the delivery catheter (24) and the inner surface of the delivery sheath (22); one lumen for the flexible retention string (52) extending distally from its fixed end (54) to the implant (10), and the other lumen for the flexible retention string (52) extending proximally back from the implant (10) to its free end (56). Although FIGS. 5A and 5B illustrate exemplary embodiments of the cross-section profiles of the delivery system (20), it should be understood by those skilled in the art that other cross section profiles can also be used to achieve the same or equivalent purpose.

Figure 6:
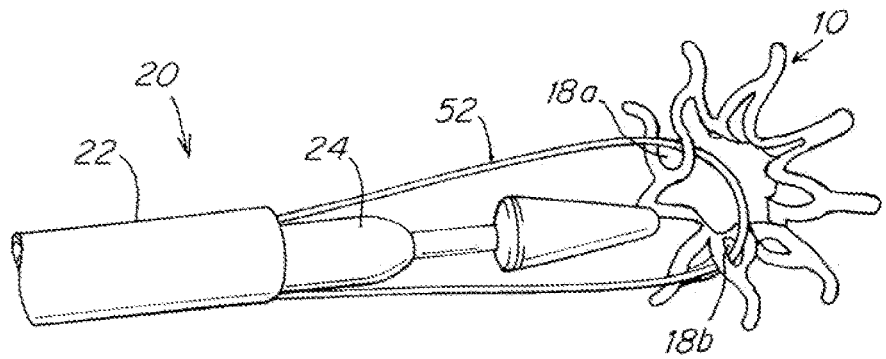
FIG. 6 is a perspective view of an exemplary medical device delivery system attaching to a deployed medical device in accordance with the present teachings.

FIG. 5D illustrates another embodiment of the present teachings, where a lumen is formed along, or parallel to, the longitude axis of the delivery catheter (24). This lumen can be configured to contain a flexible retention string (52), both extending distally from its fixed end (54) to the implant (10), and extending proximally from the implant back to its free end (56). FIG. 5C illustrates that two separate lumens are formed along, or parallel to, the longitude axis of the delivery catheter (24); one lumen for the flexible retention string (52) extending distally from its fixed end (54) to the implant (10), and the other lumen for the flexible retention string (52) extending proximally back from the implant (10) to its free end (56). Although FIGS. 5C and 5D illustrate exemplary embodiments of the cross-section profiles of the delivery system (20), it should be understood by those skilled in the art that other cross section profile can also be used to achieve the same or equivalent purpose According to one embodiment of the present teachings, the implant has a retention outlet (18), as illustrated in FIG. 3. In another embodiment of the present teachings, as shown in FIG. 6, the implant has two retention outlets (18a, 18b), positioned opposite from each other radially across a longitudinal axis of the implant (10). FIG. 6 illustrates an implant being deployed while still being retained by the flexible retention mechanism to the delivery system. In the embodiment shown in FIG. 6, the free end (56) of the flexible retention string (52) extends distally from the distal end portion of the delivery catheter (24)/sheath (22), crosses the first implant retention outlet (18a), continuously extends radially across the longitudinal axis of the implant, crosses the second retention outlet (18b), extends proximally through the lumen of the delivery catheter (24)/sheath (22), and exits from the proximal end of the delivery catheter (24)/sheath (22).

Although two implant retention outlets are shown and described in details here, it should be understood by one skilled in the art that more implant retention outlets can be used to achieve the same or equivalent implant retention purpose. According to one embodiment of the present teachings, the implant retention outlets evenly distribute across the cross-section of the implant. According to another embodiment of the present teachings, the spacing between the retention outlets varies from one to another. According to one embodiment of the present teachings, the flexible retention string extends across all retention outlets. According to another embodiment of the present teachings, the retention string extends across some of the retention outlets.

According to one embodiment of the present teachings, as illustrated in FIG. 3, the fixed end (54) of the flexible retention string (52) is attached to the delivery catheter (24)/sheath (22) by a mechanical means including a screw, a bolt, a clamp or the like; a chemical means, including an adhesive or the like; a thermal means, including ultrasonic welding, laser welding, overmolding, or the like; or other attachment means known to those skilled in the art.

Figure 7:
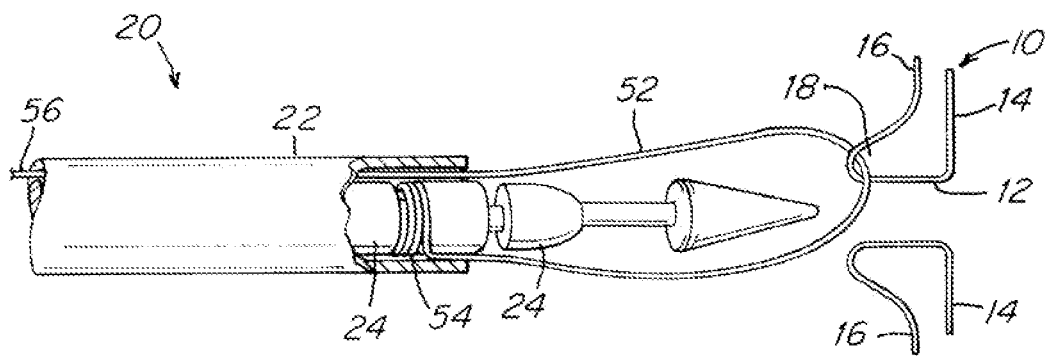
FIG. 7 is a perspective view of an exemplary medical device delivery system attaching to a deployed medical device in accordance with the present teachings.

According to another embodiment of the present teachings, as illustrated in FIG. 7, the fixed end (54) of the flexible retention string (52) attaches to the delivery catheter (24) by wrapping circumferentially around a portion of the deliver catheter (24) in one or more loops, and such loop(s) are trapped by the delivery sheath (22) during the implant deployment preventing it from unwrapping itself. During the implant delivery and deployment, the wrapped loop of the flexible retention string (52) remains trapped by the delivery sheath (22) so that the fixed end (54) of the flexible retention string (52) remains attached to the delivery catheter (24), and the implant retention string (52) maintains its hold to the implant (10). In the event that the implant deployment is not satisfactory, the delivery catheter (24) can be retracted proximally within the lumen of the delivery sheath (22), thereby pulling the flexible retention string (52) proximally, and thereby pulling implant (10) proximally back into the delivery sheath (22). Alternatively, an implant retrieval mechanism can slide over the flexible retention string (52) and capture the implant (10).

Figure 8:
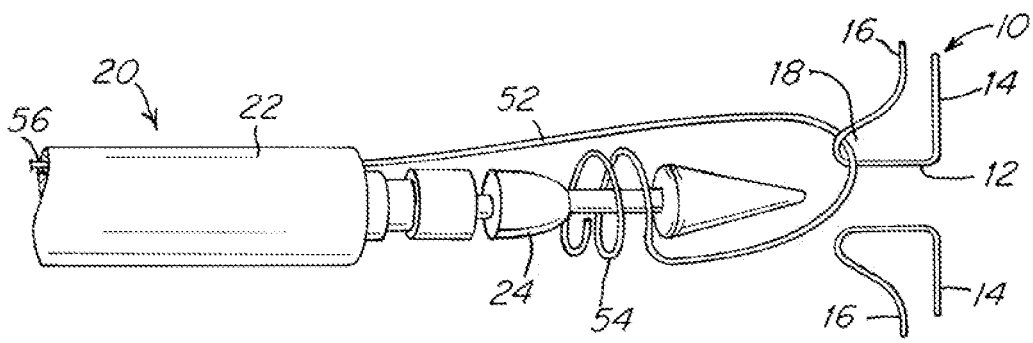
FIG. 8 is a perspective view of an exemplary medical device delivery system in FIG. 7 releasing a deployed medical device in accordance with the present teachings.
Figure 9:
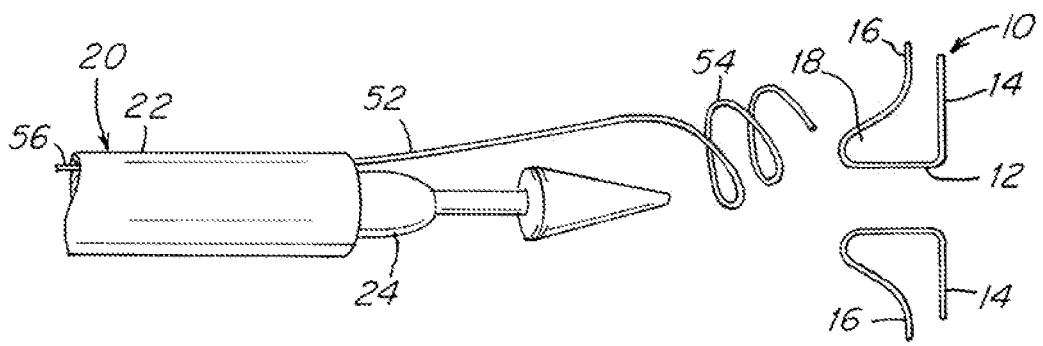
FIG. 9 is a perspective view of an exemplary medical device delivery system in FIG. 7 releasing a deployed medical device in accordance with the present teachings.

When the implant (10) is ready to be released, as illustrated in FIG. 8, the delivery sheath (22) is pulled proximally, exposing the wrapped loop of the fixed end (54) of the flexible retention string (52). As the wrapped loop unravels itself, the fixed end (54) releases its attachment to the delivery catheter (24). The free end (56) of the flexible retention string (52) is then retracted proximally, as illustrated in FIG. 9, pulling the newly freed fixed end (54) distally first, allowing the newly freed fixed end (54) of the flexible retention string (52) to be released from the implant (10) and to be completely removed from the body.

The advantage of the embodiment as described in FIG. 7 is that because the fixed end (54) of the flexible retention string (52) can be placed closer to the implant (10), the length of the flexible retention string (52) to be retracted by a clinician during the procedure is much shorter for releasing the implant (10), comparing to the embodiment described in FIG. 3.

According to one embodiment of the present teachings, where the fixed end (54) of the flexible retention string (52) is wrapped around a portion of the delivery catheter (24), the wrapped loop is trapped by the delivery sheath (22). In another embodiment of the present teachings, the wrapped loop over the delivery catheter (24) is trapped by another outer sheath that is slidably disposed over the delivery catheter (24). According to another embodiment of the present teachings, where the fixed end (54) of the flexible retention string (52) is wrapped around a portion of the delivery sheath (22), the wrapped loop is trapped by another outer sheath that is slidably disposed over the delivery sheath (22).

Still referring to FIG. 7, the circumference of the delivery catheter (24) is modified circumferentially at the place where the fixed end (54) of the flexible retention string (52) is wrapped around. Such modification allows the overall circumference of the wrapped retention string align with the adjacent surface of the delivery catheter (24), so that no extra friction is introduced when the delivery catheter (24) slides inside the lumen of the delivery sheath (22), or outer sheath. In an alternative embodiment, the overall circumference of the delivery catheter at where the retention string wrapped around is greater than that of the adjacent surface of the delivery catheter (24) so that the wrapped loop is secured by the delivery sheath or outer sheath, preventing the loop from untying itself during an implant delivery and deployment.

The present teachings also disclose other embodiments of the flexible implant retention mechanism. Now referring to FIG. 10, the flexible retention string (52) is tied to the implant (10) through the implant retention outlet (18), forming an exploding knot (58). The term "exploding knot" means a knot that can untie itself with one tug of one end of the string, leaving no tangle. According to one embodiment of the present teachings, an exploding knot includes one end of the flexible retention string (52), represented as "Fr" (i.e., free end), and the other end of the flexible retention string (52), represented as "Fi" (i.e., fixed end). Pulling on the "Fi" end of the flexible retention string would tighten the knot, and pulling on the "Fr" end of the retention string would untie the knot. Exploding knot (58) requires a balance between being tight enough to hold the implant securely and being loose enough to let the string slide through when the "Fr" end is pulled.

According to one embodiment of the present teachings, upon forming an exploding knot, both "Fi" end and "Fr" ends of the flexible retention string (52) extend proximally through the longitudinal lumen of the delivery catheter (24)/sheath (22) similar to what has been described above, and exit the proximal end of the delivery catheter (24)/sheath (22). During an implant delivery and deployment, the "Fi" end of the flexible retention string (52) is held closely so that, the exploding knot (58) is secured, the flexible retention string (52) retains the implant firmly, and the implant (10) remains in contact with the clinician. In the event that the implant deployment is not satisfactory, such flexible retention string (52) can be used to pull the implant (10) proximally back into the delivery sheath (22). Alternatively, an implant retrieval mechanism can be advanced over the flexible retention string (52) and capture the implant (10).

According to various embodiments of the present teachings, when the implant (10) is ready to be released, a clinician pulls the "Fr" end of the flexible retention string (52) proximally to untie the exploding knot (58), and then retracts the "Fr" end of the flexible retention string (52) further proximally to allow the "Fi" end of the flexible retention string (52) to extend distally through the implant retention outlet (18), releasing the implant (10) from flexible retention string (52). Alternatively, upon pulling the "Fr" end of the flexible retention string (52) proximally to untie the exploding knot (58), a clinician can then retract the "Fi" end of the flexible retention string (52) proximally and release the implant (10).

Figure 10:
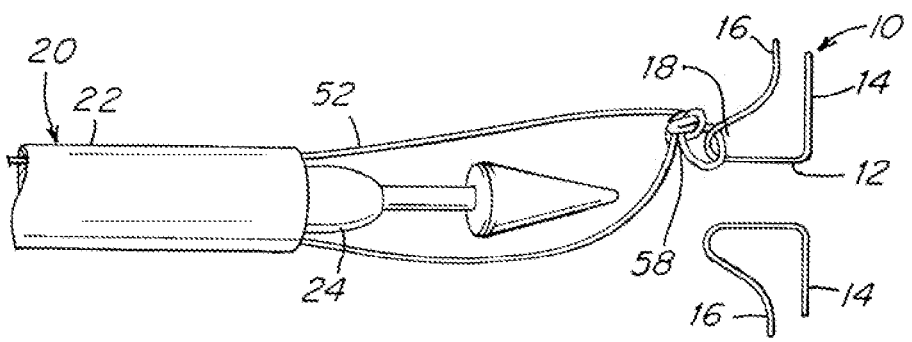
FIG. 10 is a perspective view of an exemplary medical device delivery system attaching to a deployed medical device in accordance with the present teachings.

According to one embodiment of the present teachings, as illustrated in FIG. 10, the flexible retention string (52) is tied directly to the implant (10). In an alternative embodiment, the flexible retention string (52), upon crossing the implant retention outlet (18), is tied to a portion of the delivery catheter (24) or the delivery sheath (22).

According to one embodiment of the present teachings, the "Fi" end of the flexible retention string (52) is held firmly throughout an implant delivery and deployment process. In an alternative embodiment, the "Fi" end of the flexible retention string (52) is let free at where is close to the exploding knot. In this embodiment, when the exploding knot (58) is untied by a tug on the "Fr" end of the flexible retention string (52), a clinician can further retract the "Fr" end of the flexible retention string (52) proximally, allow the "Fi" end of the retention string (52) to be released from the implant retention outlet (18), thereby releasing the implant (10). The advantage of such embodiment is that because the "Fi" end of the flexible retention string (52) is closer to the implant (10), the length of the flexible retention string (52) to be retracted by a clinician during the procedure is much shorter for releasing the implant (10), comparing to the embodiment described otherwise.

Figure 11A:
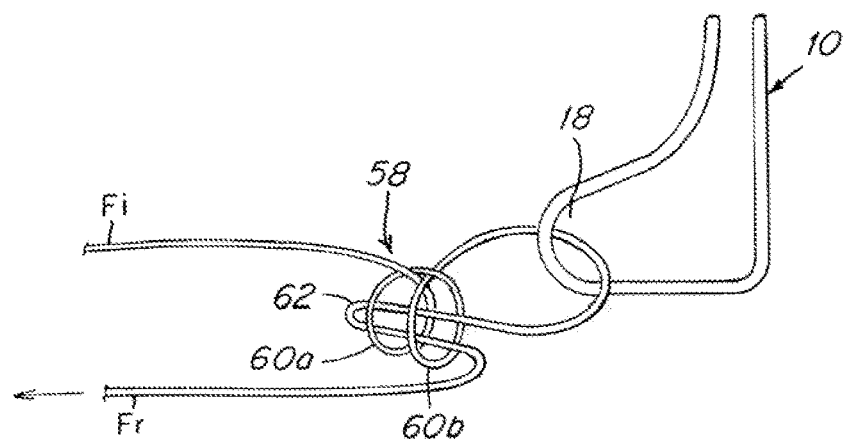
FIG. 11A is a perspective view of an exemplary implant retention mechanism in FIG. 10 attaching to a deployed medical device in accordance with the present teachings.
Figure 11B:
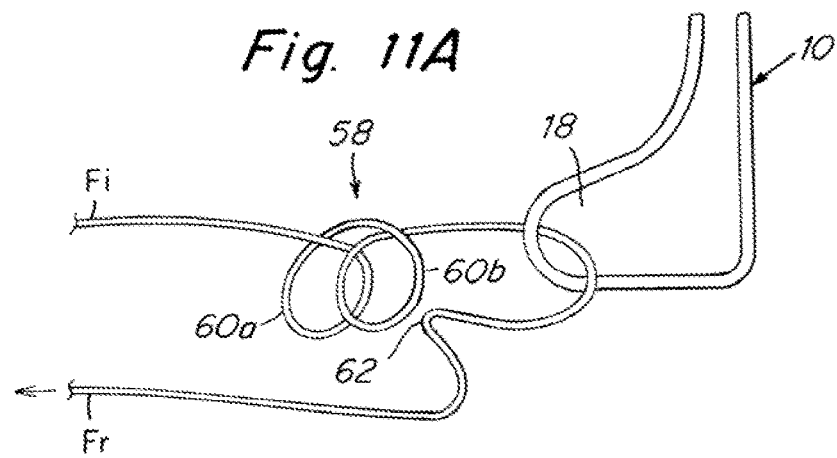
FIG. 11B is a perspective view of an exemplary implant retention mechanism in FIG. 10 releasing a deployed medical device in accordance with the present teachings.

FIGS. 11A-B illustrate the details of an example of an exploding knot (58) according to one embodiment of the present teachings. FIG. 11A illustrates an exploding knot (58) having two coils (60a, 60b) holding a double-over portion (62) of the string. The knot is tightened by pulling the "Fi" end of the string. To release the knot, as illustrated in FIG. 11B, a clinician would pull the "Fr" end of the string to pulled out the double-over portion (62) of the string from the two coils (60a, 60b), thereby untying the exploding knots (58). The clinician can then release the retained implant by proximally pulling either the "Fr" end or the "Fi" end of the flexible retention string (52).

Figure 11C:
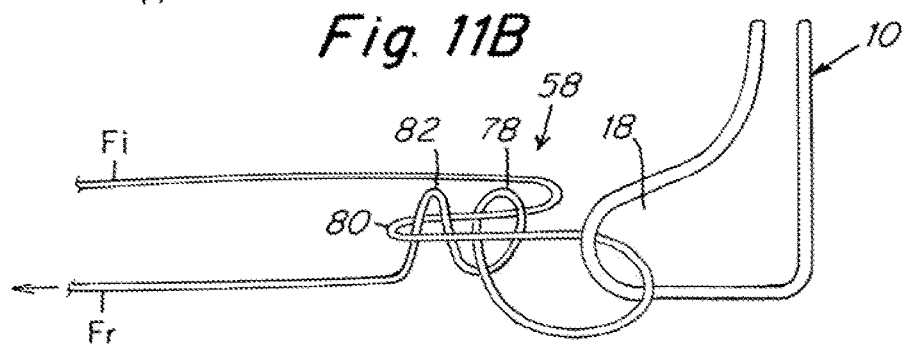
FIG. 11C is a perspective view of an exemplary implant retention mechanism in FIG. 10 attaching to a deployed medical device in accordance with the present teachings.
Figure 11D:
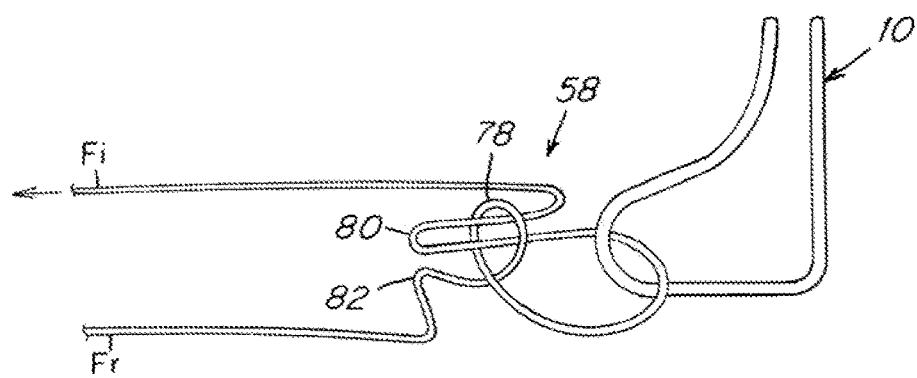
FIG. 11D is a perspective view of an exemplary implant retention mechanism in FIG. 10 releasing a deployed medical device in accordance with the present teachings.

FIGS. 11C-D illustrate the details of another example of an exploding knot (58). FIG. 11C illustrates that the knot is formed by forming a loop (78) at a portion of the flexible retention string (52) toward its "Fr" end. A portion towards the "Fi" end of the string (52) forms a first double-over (80) and extends through the loop (78). Then, the portion of the string toward the "Fr" end forms a second double-over (82) and extends through the loop of the first double-over (80). The knot (58) is tightened by pulling the "Fi" end of the string (52). To untie the knot, as illustrated in FIG. 11D, a clinician pulls the "Fr" end of the string (52) so that the second double-over portion (82) of the string (52) is pulled out of the loop of the first double-over (80). The clinician releases the retained implant (10) by pulling the "Fi" end of the flexible retention string (52) to pull the first double-over portion (80) of the string (52) out of the first loop (78). The implant is then released by proximally pulling either the "Fr" end or the "Fi" end of the retention string (52).

It should be understood that the above exemplary embodiments are only for illustrative purpose and numerous exploding knot designs can be incorporated to achieve the same or equivalent implant retention function, which are included in the present teachings.

Rigid Retention Mechanism

The present teachings also include a delivery system with a rigid implant retention mechanism. Similar to the above described flexible implant retention mechanisms, the rigid implant retention mechanism also imposes minimum or no strain to the implant so that a clinician can assess the true deployment status, i.e., that the deployment position will not be changed during or after releasing the implant. According to one embodiment of the present teachings, a rigid implant retention mechanism includes an implant retention wire which holds the implant securely during implant delivery and deployment, and allows the implant to be positioned naturally against the atrial septum conforming to the dynamic environment of the heart. The term "rigid" is used here to arbitrarily differentiate some embodiments from other embodiments, in which the implant retention mechanism in the some embodiments is relatively (e.g., slightly, moderately, or significantly) more rigid than that in the other embodiments. The terms "rigid" and "relatively rigid" are interchangeable.

According to one embodiment of the present teachings, the rigid implant retention mechanism can be used to retrieve a deployed implant by pulling the implant back into its delivery catheter/sheath or a retrieval catheter/sheath. Alternatively, the rigid implant retention mechanism can be used to guide implant retrieval by allowing an implant retrieval system to slide over the implant retention mechanism and locate/reach the implant.

As described in details below, a rigid implant retention mechanism can include an implant retention wire. While the description herein refers to wires, other terms, for example, cable or lead, are essentially interchangeable. In addition, in some embodiments, each wire, cable, or lead comprises one or more wires, cables, or leads.

According to one embodiment of the present teachings, the implant retention wire could be made of a variety of materials, including a metal, an alloy (e.g., a stainless steel or Nitinol), or a plastic.

In one embodiment of the present teachings, the cross section of the implant retention string may be circular or polygonal, such as square, or hexagonal. According to one embodiment, the implant retention wire has a uniform diameter of 0.1 mm to 1 mm throughout its entire length. Alternatively, the implant retention wire has a uniform diameter of 2 mm to 5 mm throughout its entire length. Alternatively, the implant retention wire can have a smaller diameter toward its distal end portion for increased flexibility. For example, the implant retention wire can have a gradually decreased diameter from its proximal end toward its distal end. In another embodiment of the present teachings, the implant retention wire includes a reduced diameter "neck" portion to increase the flexibility at its distal end portion. It should be understood by those skilled in the art that various profiles, cross-section designs, and various material choices for the implant retention wire can be incorporated to achieve the intended implant retention purpose as described herein without undue experimentation on the skilled artisan's part.

Figure 12:
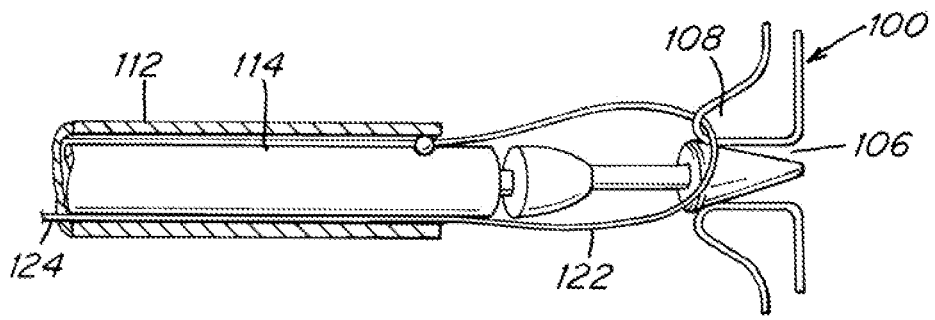
FIG. 12 is a perspective view of an exemplary medical device delivery system attaching to a deployed medical device in accordance with the present teachings.

Now referring to one embodiment of the present teachings, as illustrated in FIG. 12, a delivery system (110) with a rigid implant retention mechanism (120) is used for delivering a cardiac implant (100). FIG. 12 illustrates a cardiac implant (100) deployed in the heart (not shown) with the rigid implant retention mechanism (120) still engaging the implant (100). In this embodiment, the delivery system (110) includes a delivery sheath (112) having a distal end, a proximal end, and a longitudinal lumen extending along a longitudinal axis from its proximal end to its distal end; a delivery catheter (114) having a proximal end and a distal end and slidably disposed within the longitudinal lumen of the delivery sheath (112); and a relatively rigid implant retention mechanism (120) having an implant retention wire (122) with a fixed end (124) and a free end (126).

Referring still to FIG. 12, according to one embodiment of the present teachings, the implant retention mechanism (120) includes a wire (122) with a fixed end (124) attached to a distal end portion of the delivery catheter (114) and a free end (126) extending from the distal end portion of the delivery catheter (114), crossing a retention outlet (108) on the implant device (100), extending proximally, and being then releasably secured by the delivery system (110), for example by the delivery sheath (112) alone, the delivery catheter (114) alone, or a combination of the delivery catheter (112) and delivery sheath (114).

In this exemplary embodiment, the implant device (100) has a longitudinal lumen (106) extending from one end of the body portion (102) to the other end of the body portion (102), so that the body portion (102) of the implant (100) has an outer surface which faces, and contacts, the septum at atrial aperture, and an inner surface which faces the longitudinal lumen (106). In one embodiment of the present teachings, the implant retention outlet (108) is located on the body portion (102) of the implant (100). According to one embodiment of the present teachings, the free end (126) of the rigid retention wire (122) extends along the outer surface of the body portion (102), crosses the implant retention outlet (108), extends proximally along the inner surface of the body portion (102), through the longitudinal lumen (106) of the body portion (102) of the implant (100), further proximally through the longitudinal lumen of the delivery sheath (112), and is releasably secured by the delivery system (110). In an alternative embodiment, the free end (126) of the rigid retention wire (122) extends along the outer surface of the body portion (102), crosses the implant retention outlet (108), extends proximally along the inner surface of the body portion (102), through the longitudinal lumen (106) of the body portion (102) of the implant (100), further proximally through the longitudinal lumen of the delivery sheath (112), and is releasably secured by the delivery system (110).

According to another embodiment, where the implant retention outlet (108) is located on a proximal flange (104) of the implant (100). For example, as the implant device is stowed in its elongated profile, the proximal flanges (104) are retracted radially, forming an elongated proximal flange portion (104) with a longitudinal lumen, so that the elongated proximal flange portion (104) of the implant (100) has an outer surface which, when deployed, faces, and contacts, the septum at atrial aperture, and an inner surface which, when deployed, faces the right atrium. In one embodiment, the free end (126) of the rigid retention wire (122) extends along the outer surface of the elongated proximal flange portion (104), crosses the implant retention outlet (108), extends proximally along the inner surface of the elongated proximal flange portion (104), further proximally through the lumen of the delivery sheath (112), and is releasably secured by the delivery system (110). According to an alternative embodiment, the free end (126) of the rigid retention wire (122) extends along the inner surface of the elongated proximal flange portion (104), crosses the implant retention outlet (108), extends proximally along the outer surface of the elongated proximal flange portion (104), further proximally through the lumen of the delivery sheath (112), and is releasably secured by the delivery system (110).

Referring to FIG. 12, according to one embodiment of the present teachings, the flexibility of the implant retention wire (122) allows a clinician to maintain contact with the implant (100), without introducing strain on the implant (100), thereby allowing an implant (100) to conform to the anatomy of the atrial septum. Such embodiments allow a clinician to assess the true status of an implant deployment before releasing the implant. Such embodiments also eliminate the risk of shifting the implant position when the implant is released from the delivery system (110). In the event that an implant deployment is not satisfactory, a clinician can advance a device retrieval mechanism, for example, by sliding it over the retention wire (122), to retrieve the implant (100). In another embodiment, a clinician can retrieve the implant (100) by retracting implant retention wire (122) proximally, thereby pulling the implant (100) back into a delivery/retrieval sheath from the distal end.

Figure 13:
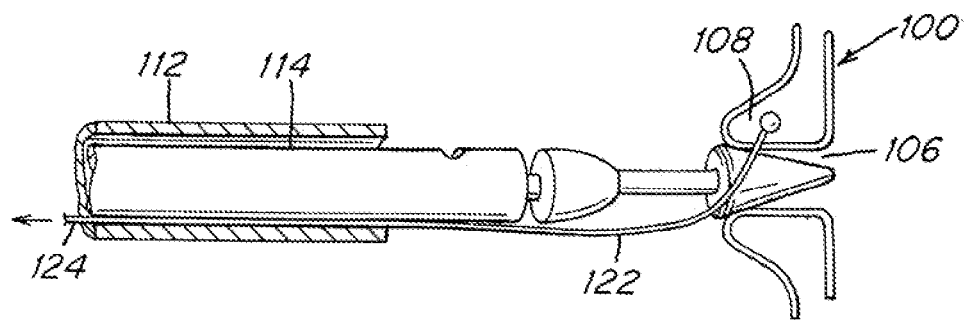
FIG. 13 is a perspective view of an exemplary medical device delivery system in FIG. 12 releasing a deployed medical device in accordance with the present teachings.

In the event that the deployment is successful, the clinician can distally extend the delivery catheter (114) and/or proximally retract the delivery sheath (112) to slide a distal portion of the delivery catheter (114) outside of the deliver sheath (112). As shown in FIG. 13, as the distal portion of the delivery catheter (114) slides outside of the delivery sheath (112), the free end (126) of the retention wire (122) is released from its attachment to the delivery catheter (114). The implant (100) is then released from the retention wire (122) by the clinician retracting the retention wire (122) proximally, releasing the free end (126) of the wire (122) from the implant retention outlet (108), and freeing the implant (100) completely.

According to one embodiment of the present teachings, the fixed end (124) of the retention wire (122) is attached to the delivery catheter (114) by a mechanical means, including a screw, a bolt, or the like; a chemical means, including an adhesive and the like; a thermal means, including ultrasonic welding, laser welding, overmolding, or the like; or other suitable attachment means.

FIGS. 14 A-D illustrate various embodiments of the releasable attachment of the free end (126) of the retention wire (122) to the delivery system (110). FIG. 14A illustrates a releasable securement to the free end (126) of the retention wire (122) in the gap between the inner surface of the delivery sheath (112) and the delivery catheter (114). During an implant delivery and deployment, the free end (126) of the retention wire (122) is secured by the delivery sheath (112) sliding over the wire and that delivery catheter (114).

According to yet another embodiment of the present teachings, the retention wire (122) has an elasticity or a shape memory, allowing the free end (126) of the retention wire to be constrained by the delivery sheath (112) during implant delivery and deployment, and allowing the retention wire (122) to resume a relatively straight profile after its free end (126) released from the delivery sheath (112). In such an embodiment, the inner dimension of the delivery sheath (112) can be slightly smaller than the combined outer circumference of the retention wire (122) and the delivery catheter (114). Alternatively, the inner dimension of the delivery sheath (112) can be the same as the outer dimension of the combined outer circumference of the retention wire (122) and the delivery catheter (114). In another embodiment, the inner dimension of the delivery sheath (112) can be slightly greater than the combined outer circumference of the retention wire (122) and the delivery catheter (114).

According to another embodiment of the present teachings, the releasably securement of the free end (126) of the retention wire (122) to the delivery system (110) is achieved by the elasticity or the shape memory property of the retention wire (206). In an alternative embodiment, the releasably securement of the free end (126) of the retention wire (122) to the delivery system (110) is achieved by a dimensional interference force. To achieve this securement, the overall outer circumference of the wire (122) combining with the delivery catheter (114) should be slightly greater than the inner dimension of the delivery sheath (112), so that when the delivery sheath (112) slides over the delivery catheter (114), the free end (126) of the wire (122) is firmly held by the interference. In one embodiment, the portion of the delivery catheter (114), where the free end (126) of the retention wire (122) ends, has an indentation. Such indentation allows the combined outer circumference of the wire (122) and delivery catheter (114) be the same, or slightly smaller, or slightly greater than the delivery sheath (112).

Figure 14A:
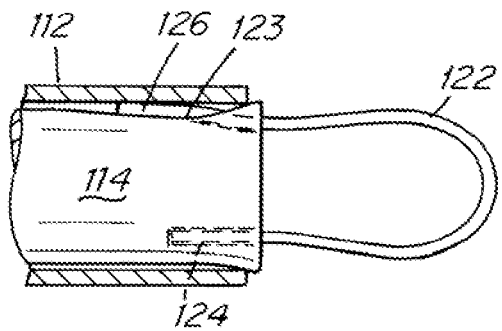
FIG. 14A is a perspective view of an exemplary implant retention mechanism in FIG. 12 attaching to a deployed medical device in accordance with the present teachings.

According to an alternative embodiment of the present teachings, as illustrated in FIG. 14A, the portion of the outer surface of the delivery catheter (114) where the free end (126) of the retention wire (122) ends is modified so that the overall outer circumference of the delivery catheter (114) combining with the retention wire (122) aligns with the proximal adjacent outer surface of the delivery catheter (114). The outer circumference of the distal portion of the delivery catheter (114) to the modified portion of the delivery catheter (114) remains unchanged. In one embodiment, this portion (123) of the delivery catheter (114) combining with the retention wire (122) creates an interference with the inner dimension of the delivery sheath (112), thereby securing the free end (126) of the retention wire (122).

In one embodiment of the present teachings, the cross-section of the retention wire (122) remains the same from its free end (126) to its fixed end (124). In other embodiments, the free end (126) of the retention wire (122) has a larger outer profile than the remaining portion of the retention wire (122). The larger profile of the free end (126) can be in the shape of a ball, a cone, a coil, or other forms which is configured to achieve the same purpose of the present teachings.

Figure 14B:
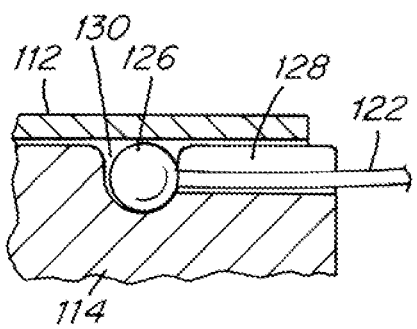
FIG. 14B is a perspective view of an exemplary implant retention mechanism in FIG. 12 attaching to a deployed medical device in accordance with the present teachings.
Figure 14C:
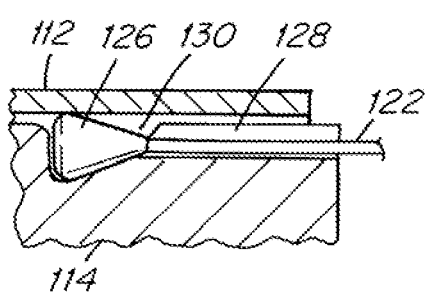
FIG. 14C is a perspective view of an exemplary implant retention mechanism in FIG. 12 attaching to a deployed medical device in accordance with the present teachings.
Figure 14D:
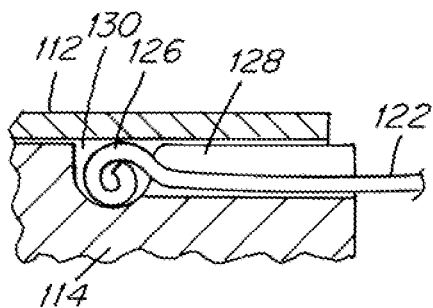
FIG. 14D is a perspective view of an exemplary implant retention mechanism in FIG. 12 attaching to a deployed medical device in accordance with the present teachings.

FIGS. 14B-14D illustrate other approaches for securing the free end (126) of the retention wire (122). In all three examples, as illustrated in FIGS. 14B-14D, the free end (126) of the retention wire (122) has an enlarged outer profile. A key way (128) and a key slot (130) is formed on the outer surface of the delivery catheter (114). The free end (126) of the retention wire (122), after crossing the implant retention outlet (108), extends proximally so that the enlarged free end (126) of the retention wire (122) rests inside the key slot (130), and the portion next to the enlarged free end (126) of the retention wire (122) rests inside the key way (128). During an implant delivery and deployment, the distal end portion of the delivery sheath (112) slides over the distal end portion of the delivery catheter (114) and encapsulates the free end (126) of the retention wire (122).

In one embodiment, the free end (126) of the retention wire (122) is secured because the outer dimension of the free end (126) of the retention wire (122) is greater than the key slot (130) on the outer surface of the delivery catheter (114), so that the combined outer dimension of the retention wire (122) and delivery catheter (114) remains greater than the inner dimension of the delivery sheath (112), thereby creating an interference securement. In another embodiment, the outer profile of the free end (126) of the retention wire (122) is greater than the portion of the retention wire (122) next to the free end (126), and the corresponding dimension of the key slot (130) is greater than the key way (128). So, when the delivery sheath (112) slides over the key way (128) portion of the delivery catheter (114), the enlarged free end (126) of the retention wire (122) is trapped even when the combined outer dimension of the free end (126) of the retention wire (122) and delivery catheter (114) is not greater than the inner dimension of the delivery sheath (112).

FIG. 14B illustrates a ball configuration of the enlarged free end (126) of the retention wire (122) and a socket configuration of the key slot (130) on the delivery catheter (114) for holding the ball. FIG. 14C illustrates a cone configuration of the enlarged free end (126) of the retention wire (122) with the largest dimension at the very end and a matching cone shaped key slot (130) for holding the cone. FIG. 14D illustrates an enlarged coiled tip at the free end (126) of the retention wire (122) and a matching key slot (130) on the surface of the delivery catheter (114) for holding the coiled tip.

Referring to the embodiments as illustrated in FIG. 14A-14D, according to one embodiment of the present teachings, when a successfully deployed implant is ready to be release, the clinician withdraws the delivery sheath (112) proximally, completely exposing the free end (126) of the implant retention wire (122). As the free end (126) of the retention wire (122) is freed from constrain, and the retention wire resumes its predefined relatively straight profile, the clinician withdraws the delivery catheter (114) further proximally, thereby releasing the free end (126) of the retention wire (122) from the implant retention outlet (108), thereby releasing the implant (100).

Still referring to the embodiments illustrated in FIGS. 14A-14D, according to one embodiment of the present teachings, the cross-section of the delivery catheter (114) is modified for the implant retention wire (122). Similar to the embodiments shown in FIG. 5B, two lumens are formed between the delivery sheath (112) and the delivery catheter (114) with one for the retention wire (122) extending from its fixed end (124) to the implant (100), and the other for the retention wire (122) extending from its freed end (126) to the implant (100). In another embodiment, only one lumen is formed between the delivery sheath (112) and the delivery catheter (114), which allow both the retention wire (122) extending from its fixed end (124) to the implant (100), and the retention wire (122) extending from the implant (100) to its freed end (126).

Figure 15:
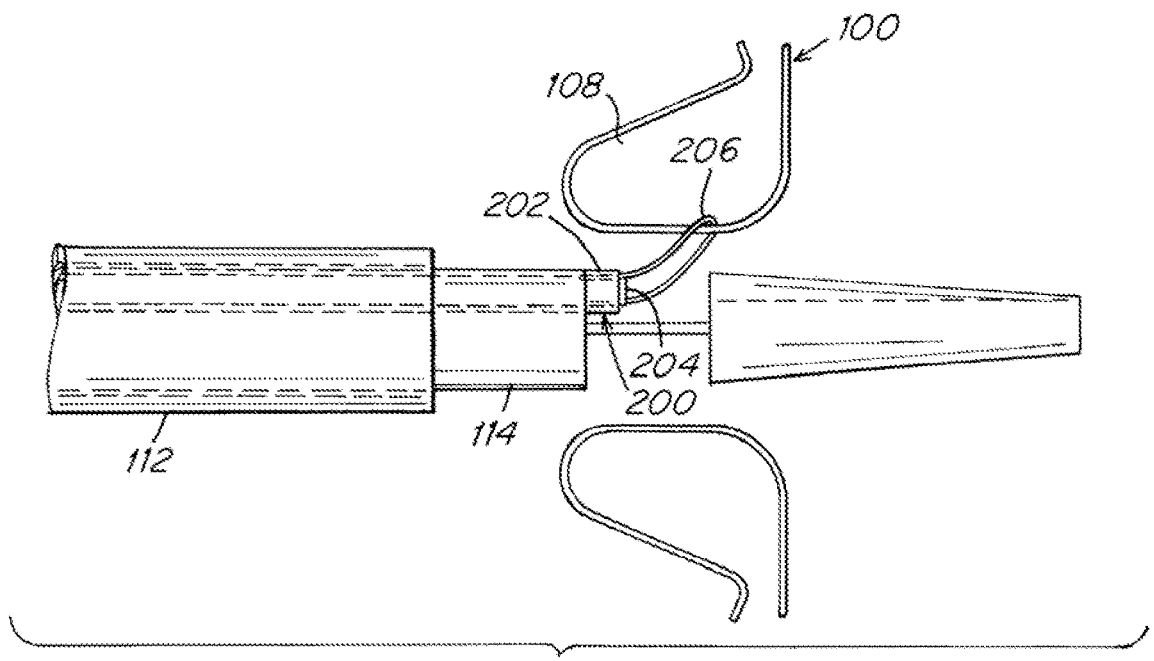
FIG. 15 is a perspective view of an exemplary medical device delivery system attaching to a deployed medical device in accordance with the present teachings.

According to yet another embodiment of the present teachings, a lumen (210) formed between the delivery sheath (112) and the delivery catheter (114) holds an implant retention mechanism (200) including an elongated tube (202), an implant retention mandrel (204) and an implant retention wire (206). As illustrated in FIG. 15, the elongated tube (202) is slidably disposed within the lumen (210) firmed by the delivery sheath (112) and the delivery catheter (114), the elongated implant retention mandrel (204) is slidably disposed within the elongated tube (202), and the implant retention wire (206) having a fixed end connected to a distal end portion of the implant retention mandrel (204). The implant retention wire (206) also has a free end which is releasably secured by the implant retention mechanism (200), such as between the elongated tube (202) and the implant retention mandrel (204).

Similar to what is described above and referring to FIG. 12, the implant retention wire (206) retains the implant at its retention outlet. The above-described details referring FIGS. 12-14 are therefore incorporated herein. FIG. 15 illustrates a deployed implant retained by a retention wire. As shown in this figure, the implant is free from constrain by the delivery sheath and the delivery catheter and is attached to the implant retention wire (206) with its free end stowed within the elongated tube (202) of the implant retention mechanism (200).

Figure 16:
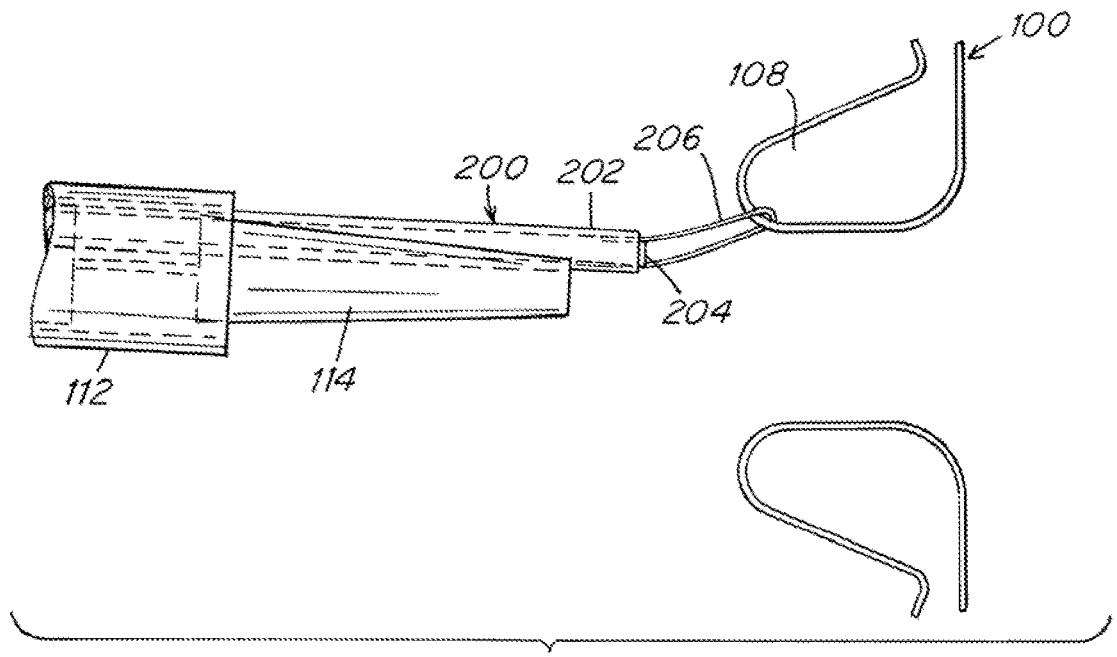
FIG. 16 is a perspective view of an exemplary medical device delivery system in FIG. 15 attaching to a deployed medical device in accordance with the present teachings.

According to one embodiment of the present teachings, as illustrated in FIG. 16, as the implant retention mechanism (200) extends distally with its distal end passing the distal end of the delivery sheath (112) or delivery catheter (114), the implant retention wire (206) retains the deployed implant. Such an embodiment allows a maximum freedom of movement for the implant such as a deployed implant can be positioned naturally against the septum.

In the event that the implant deployment is not satisfactory, a clinician can retract the entire implant retention mechanism (200) proximally with the free end of the retention wire (206) remaining inside the elongated tube (202), thereby pulling the implant back into the delivery sheath.

Figure 17:
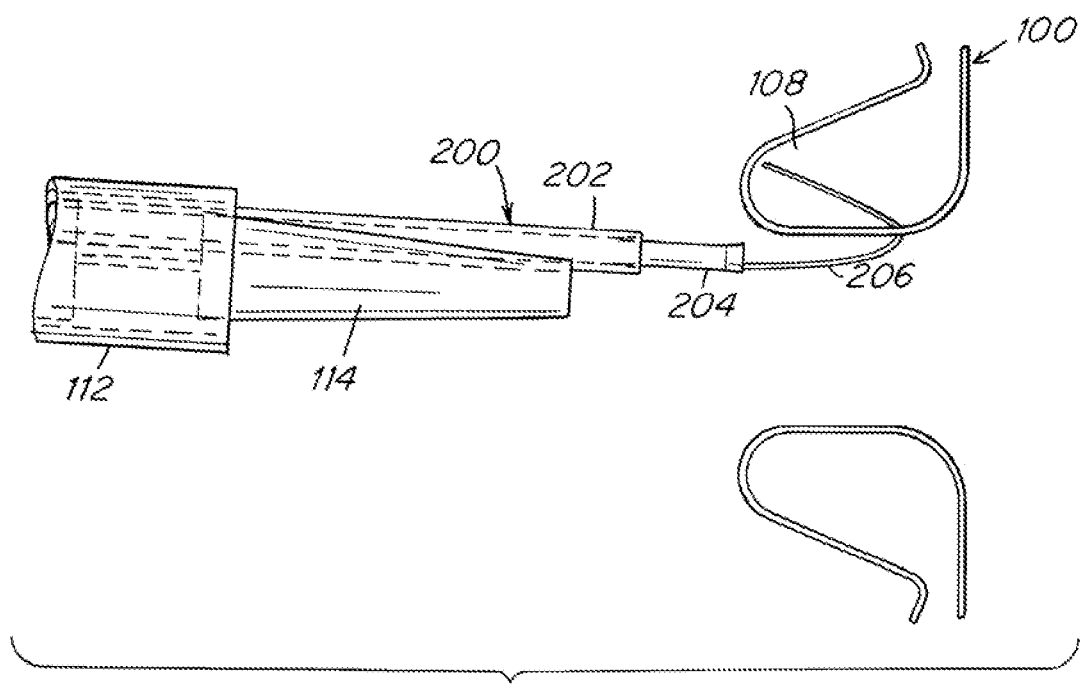
FIG. 17 is a perspective view of an exemplary medical device delivery system in FIG. 15 releasing a deployed medical device in accordance with the present teachings.

Now referring to FIG. 17, when the implant is ready to be released, a clinician retracts the elongated tube (202) proximally while holding the retention mandrel (204) steady, releases the free end of the implant retention wire (206) from its constraint. Alternatively, the implant retention mandrel (204) can be pushed distally while the elongated tube (202) is held steady, thereby exposing the free end of the implant retention wire (206). Upon the free end of the retention wire (206) being released, the retention wire resumes its predefined relatively straight profile. A clinician can then retract the implant retention mandrel (204) further proximally, allowing the free end of the retention wire (206) to be released from the implant retention outlet and thereby releasing the implant.

With reference to FIGS. 15-17, according to one embodiment of the present teachings, the fixed end of the retention wire (206) is attached to the implant retention mandrel (204) by a mechanical means, including a screw, a bolt, or the like;

a chemical means, including an adhesive or the like; a thermal means, including ultrasonic welding, laser welding, overmolding, or the like; or other suitable attachment means. In addition, similar to the above described and with reference to FIGS. 12-14, according to another embodiment of the present teachings, the releasable securement of the free end of the retention wire (206) by the elongated tube (202) is achieved by either an interference force or the elasticity or the shape memory property of the retention wire (206). The above-described details with reference to FIGS. 12-14 are therefore incorporated herein. Furthermore, similar to the above-described and with reference to FIGS. 12-14, a distal end portion of the implant retention mandrel (204) can be modified in such a way to accommodate the releasable securement of the free end of the retention wire (206). The above-described details with reference to FIGS. 12-14 are therefore incorporated herein.

Figure 18:
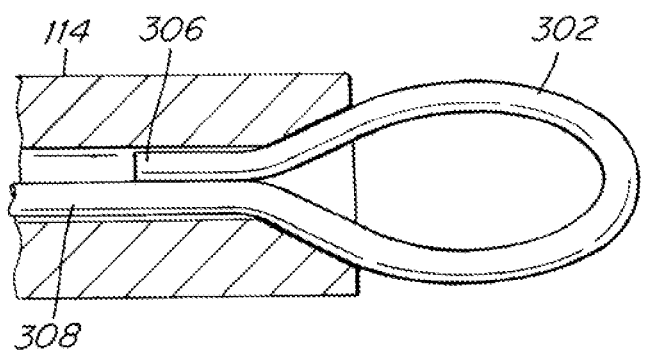
FIG. 18 is a perspective view of an exemplary implant retention mechanism attaching to a deployed medical device in accordance with the present teachings.

Now referring to another embodiment of the present teachings, as illustrated in FIG. 18, an implant retention mechanism (300) includes an implant retention wire (302) and a control (not shown). In this embodiment, the implant retention wire (302) has a proximal end (304) (not shown), a free end (306), and an elongated body (308) extending from its proximal end (304) to its free end (306). According to one embodiment of the present teachings, such implant retention wire (302) is slidably disposed within a longitudinal lumen of the delivery catheter. Alternatively, such implant retention wires (302) are slidably disposed within a longitudinal lumen of the delivery sheath side by side to the delivery catheter. As illustrated in FIG. 18, the proximal end (304) of the retention wire (302) extends outside of the proximal end (304) of the delivery sheath/catheter, and connects to the control of the implant retention wire (302).

Still referring to FIG. 18, during an implant delivery and deployment, the free end (306) of the retention wire (302) extends distally, crosses the implant retention outlet, turns and extends proximally, and enters the longitudinal lumen of the delivery catheter/sheath from its distal end. According to one embodiment of the present teachings, the resilient, elastic, or shape memory property of the retention wire allows the free end (306) of the retention wire (302) to remain inside the lumen during implant delivery and deployment. In other embodiment, the resilient, elastic, or shape memory property of the retention wire allows the retention wire to resume its predefined relatively straight profile.

Similar to what has been described above as referring to FIG. 12, the implant retention wire (302) retains the implant at its retention outlet. The above described details of the embodiment are therefore incorporated herein. According to one embodiment of the present teachings, when a deployed implant is to be retrieved, a clinician uses the control of the implant retention mechanism (300), retracts the implant retention wire (302) back into delivery catheter/sheath. According to another embodiment of the present teachings, a retrieval mechanism can be incorporated with the delivery system and the implant retention mechanism for retrieving the deployed implant.

When a deployed implant is ready to be released, according to one embodiment of the present teachings, the implant retention wire (302) extends distally until its free end (306) beyond the distal end of the delivery catheter/sheath. As the free end (306) of the retention wire (300) exits the distal end of the delivery catheter/sheath, the distal portion of the retention wire (302) is straightened due to the resilient, elastic, or shape memory property. A clinician then retracts the retention wire (302) further proximally, allowing the free end (306) of the retention wire (302) to be released from the implant retention outlet, thereby releasing the implant.

Figure 19:
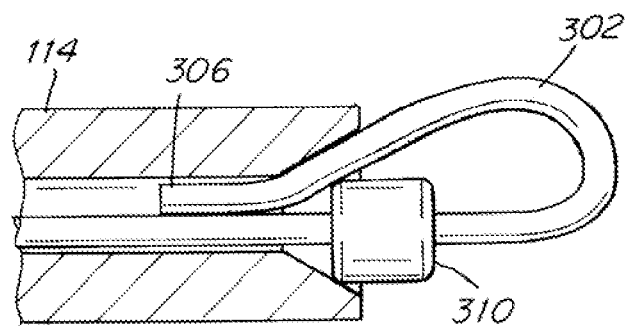
FIG. 19 is a perspective view of an exemplary implant retention mechanism attaching to a deployed medical device in accordance with the present teachings.

FIG. 19 illustrates another embodiment of the present teachings where a bulge (310) is presented on a distal end portion of the retention wire (302) close to where the retention wire (302) crosses the implant retention outlet. As seen in FIG. 19, a bulge (310) is proximal to the retained implant and on the proximal end (304) side of the retention wire (302). Alternatively, the bulge (310) of the retention wire (302) can be on the free end (306) side of the retention wire (302). In various embodiments of the present teachings, the bulge (310) of the retention wire (302) has a greater profile than the inner lumen of the delivery catheter/sheath. Thus, the bulge (310) of the retention wire (302) creates an additional securement during an implant delivery and deployment. In yet another embodiment, the bulge (310) can have feature to capture free end (306) of retention wire (302).

According to one embodiment, the bulge is formed by extra material deposited on the retention wire by mechanism means, chemical means or thermal means; or an integrated part of the retention wire itself.

Figure 20:
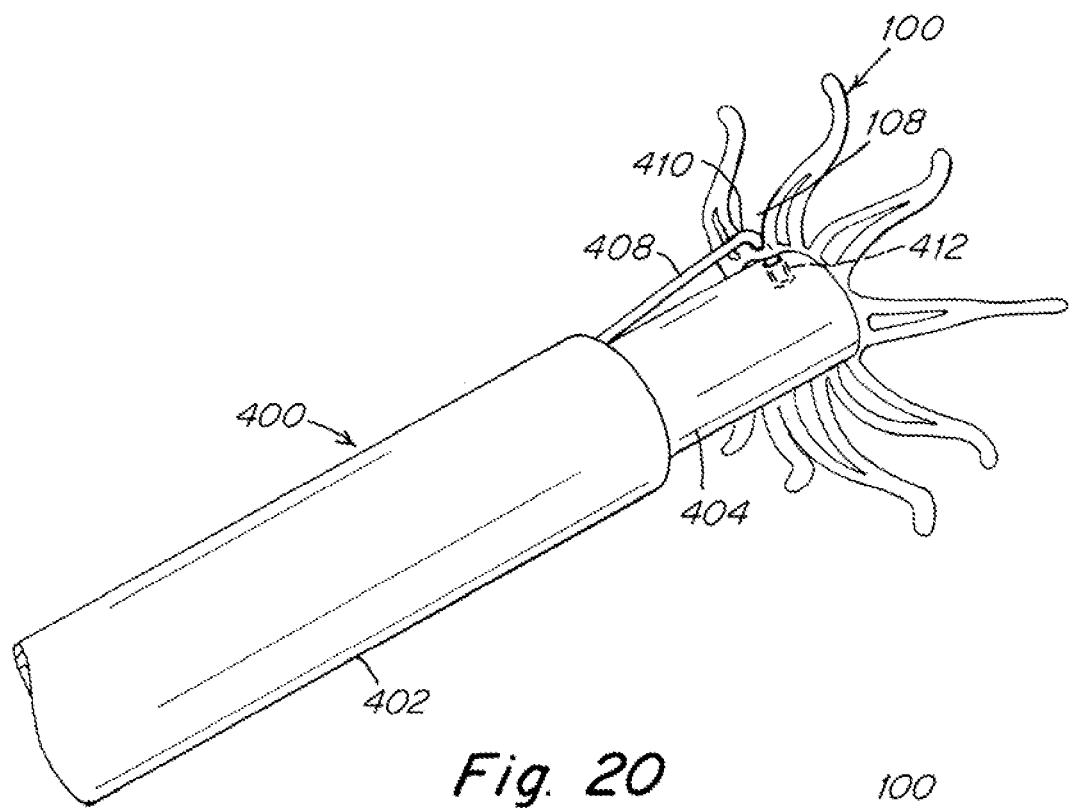
FIG. 20 is a perspective view of an exemplary medical device delivery system attaching to a deployed medical device in accordance with the present teachings.
Figure 21:
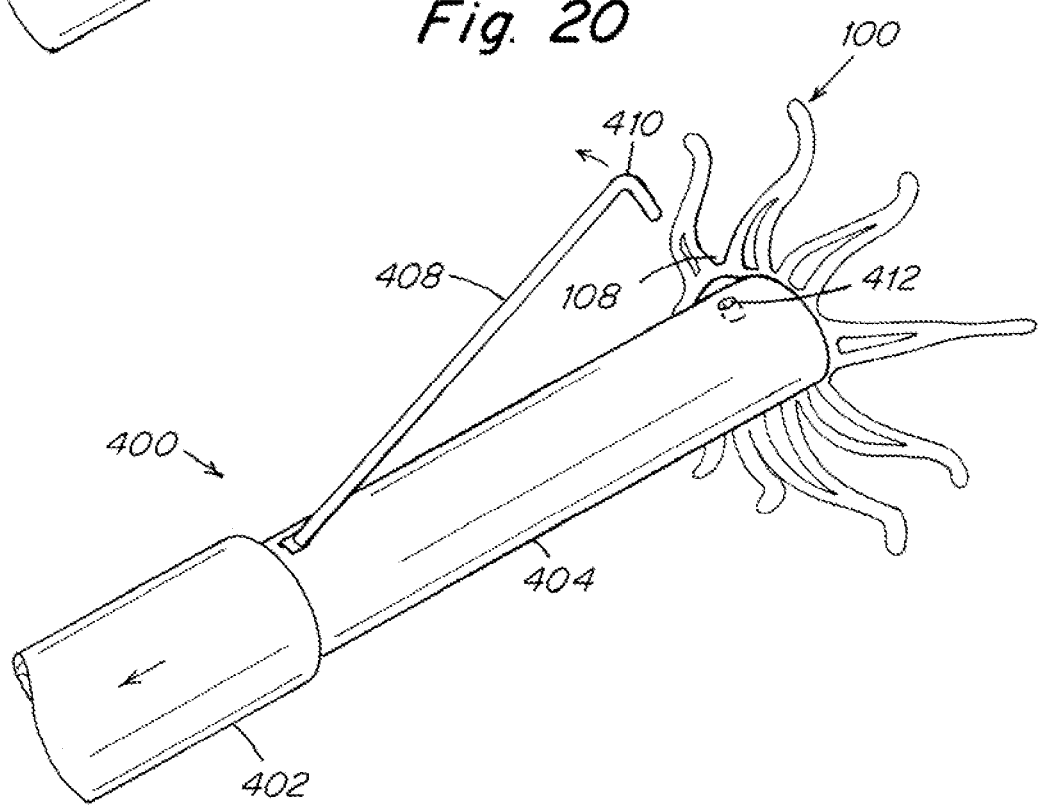
FIG. 21 is a perspective view of an exemplary medical device delivery system in FIG. 20 releasing a deployed medical device in accordance with the present teachings.

Now referring to another embodiment of the present teachings, as illustrated in FIGS. 20-21, where the implant is retained via a retention wire hook. Similar to what has been described in detail with reference to FIG. 12, in this embodiment, a delivery system includes a delivery sheath having a distal end, a proximal end, and a longitudinal lumen extending along a longitudinal axis from its proximal end to its distal end; a delivery catheter having a proximal end and a distal end and slidably disposed within the longitudinal lumen of the delivery sheath; and rigid implant retention mechanism used for retaining an implant. FIG. 20 only illustrates a distal portion of the delivery system 400, with a delivery catheter (404) slidably disposed within the longitudinal lumen of the delivery sheath (402), and an implant retention mechanism retaining a deployed implant through the implant retention outlet.

In this exemplary embodiment, similar to embodiments described in detail above, the implant has a longitudinal lumen extending from one end of the body portion to the other end of the body portion, so that the body portion of the implant has an outer surface which faces, and contacts, the septum at atrial aperture, and an inner surface which faces the longitudinal lumen. In one embodiment of the present teachings, the implant retention outlet is located on the body portion of the implant. In an alternative embodiment, the implant retention outlet is located on the proximal flanges of the implant. In yet another embodiment, the implant retention outlet is located on the distal flanges of the implant. In one embodiment of the present teachings, during implant delivery, the implant is stretched to an elongated delivery profile, with a proximal portion of the implant slidably disposed over a distal portion of the delivery catheter.

The implant retention mechanism, illustrated in FIG. 20, includes a retention wire (408) having a proximal end (not shown) and a distal bend (410), and a retention wire cavity (412), for receiving the distal bend end of the retention wire, on a distal end portion of the delivery catheter (404). According to one embodiment of the present teachings, the proximal end of the retention wire connects to the delivery catheter (404) by a mechanical means, for example, a screw, a bolt, or the like; a chemical means, for example, an adhesive or the like; a thermal means, for example, ultrasonic welding, laser welding, overmolding, or the like; or other suitable attachment means. Alternatively, the proximal end of the retention wire extends proximally inside the longitudinal lumen of the delivery sheath, and exits the proximal end of the delivery sheath. The retention wire can have a radial bend (410) at its distal end toward the longitudinal axis of the delivery catheter and/or implant. During an implant delivery and deployment, the end of the distal bend (410) of the retention wire (408) extends along the outer surface of the elongated implant, crosses the implant retention outlet on the implant, and reaches the retention wire cavity (412) on the delivery catheter (404). According to one embodiment of the present teachings, the retention wire cavity (412) forms an angle of 5° to 90° with the longitudinal axis of the delivery catheter (404).

According to one embodiment of the present teachings, the implant retention wire (408) has a strained "stowed" configuration and a relaxed radially expanded configuration. In its stowed configuration, the delivery sheath slides over the implant retention wire (408) so that the distal bend (410) of the retention wire (408) remains inside the wire retention cavity (412), thereby allowing the implant retention mechanism retains the implant. In its relaxed radially expanded configuration, the distal bend (410) of the retention wire (408) expands radially outward, releasing the end of the distal bend (410) of the retention wire (408) from the retention wire cavity (412) and the implant retention outlet, thereby releasing the implant from its attachment to implant retention mechanism.

According to one embodiment of the present teachings, to achieve its strained "stowed" configuration, the entire retention wire (408) including its distal bend (410) is slidably disposed within the delivery sheath (402). In an alternative embodiment, to achieve its strained "stowed" configuration, only a proximal portion of the retention wire (408) is disposed within the delivery sheath (402).

According to one embodiment of the present teachings, to achieve its relaxed radially expanded configuration, the entire retention wire (408) including its proximal end is exposed outside of the delivery sheath (402). Alternatively, to achieve its relaxed radially expanded configuration, only a distal portion of the retention wire (408) is exposed outside of the delivery sheath (402).

According to an exemplary delivery system, the delivery sheath (402) includes a major longitudinal lumen for the delivery catheter (404) and a separate side retention wire lumen (406) for the retention wire (408) to be slidably disposed within. According to this exemplary delivery system, the delivery catheter (404) is slidably disposed within the major longitudinal of the delivery sheath (402) and the retention wire (408) is slidably disposed within the side lumen (406). In an alternative embodiment, the delivery sheath (402) has only one longitudinal lumen where both the delivery catheter (404) and the retention wire (408) are disposed within. According to one embodiment of the present teachings, the retention wire has a size of 0.010", 0.011", 0.014", 0.018", 0.021", 0.028", 0.035", 0.038", 0.042" or 0.045". In other embodiments of the present teachings, the retention wire has a size in the range of 0.010" and 0.045".

As illustrated in FIG. 20, the implant retention wire (408) retains the implant at its retention outlet as an implant is deployed. As seen in this figure, the implant is free from strain introduced by the delivery sheath and the delivery catheter. Such an embodiment allows a maximum freedom of movement of the implant, thereby allowing a deployed implant to be positioned naturally against/in the septum. At this point, if a clinician decides that the implant deployment is not satisfactory, he/she can retract the entire implant retention mechanism, including the delivery catheter (404), implant retention wire (408) with its distal bend end remaining inside the retention wire cavity (412), proximally, thereby pulling the implant proximally back into the delivery sheath (402).

Now referring to FIG. 21, when the implant is ready to be released, a clinician retracts the delivery sheath (402) proximally while holding the delivery catheter (404) steady, allowing the retention wire (408) resume its relaxed radially expanded configuration. Alternatively, the implant retention mechanism including the delivery catheter (404) and implant retention wire (408) is pushed distally while the delivery sheath (402) is held steady, allowing the retention wire (408) resume its relaxed radially expanded configuration. As the retention wire (408) resuming its relaxed radially expanded configuration, the distal bend of the implant retention wire (408) extends radially outward, releases from the retention cavity on the delivery catheter (404) and implant retention outlet, and the implant is thereby released from the implant retention mechanism. At this point, the delivery system along with implant retention mechanism can be removed from the body.

Figure 22:
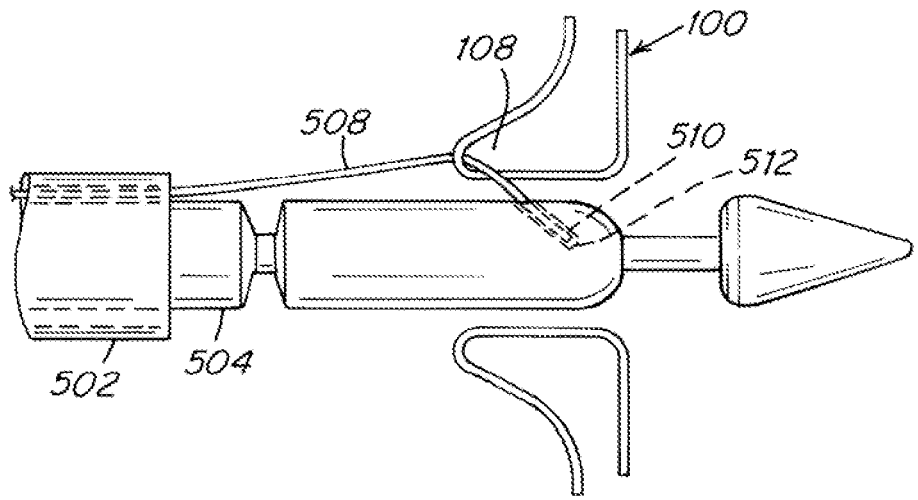
FIG. 22 is a perspective view of an exemplary medical device delivery system attaching to a deployed medical device in accordance with the present teachings.
Figure 23:
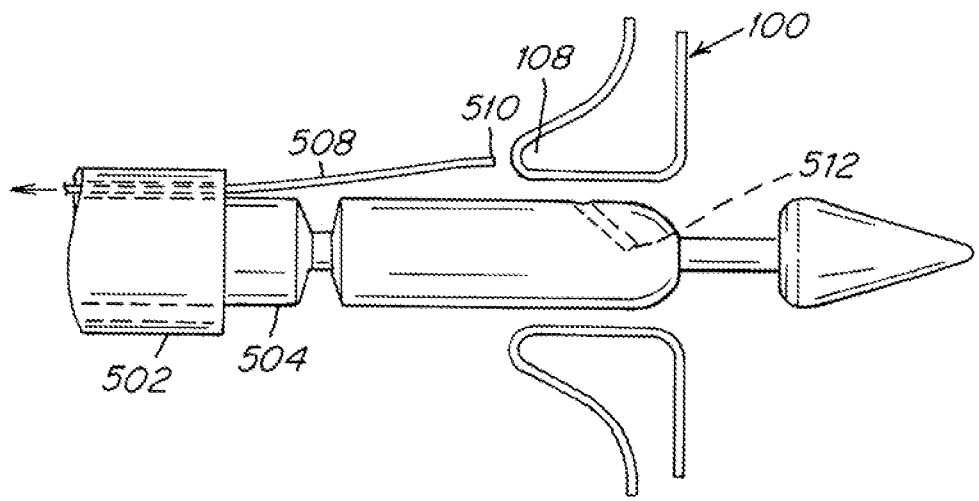
FIG. 23 is a perspective view of an exemplary medical device delivery system in FIG. 22 releasing a deployed medical device in accordance with the present teachings.

Now referring to FIGS. 22-23, the implant can be retained via other exemplary embodiments of the retention wire. The embodiment illustrated in FIG. 22 has a similar delivery system and implant configuration to what has been described above with reference to FIG. 20. The above-described details referring FIGS. 20-21 are therefore incorporated herein.

FIG. 22 only illustrates a distal portion of the delivery system (500), with a delivery catheter (504) slidably disposed within the longitudinal lumen of the delivery sheath (502), and an implant retention mechanism retaining a deployed implant through the implant retention outlet. The implant retention mechanism, illustrated in FIG. 22, includes a retention wire (508) having a proximal end (not shown) and a distal end (510), and a retention wire cavity (512), for receiving the distal end (510) of the retention wire (508), on a distal end portion of the delivery catheter (504). According to one embodiment of the present teachings, the proximal end of the retention wire connects to the delivery catheter (504) by a mechanical means, for example, a screw, a bolt, or the like; a chemical means, for example, an adhesive or the like; a thermal means, for example, ultrasonic welding, laser welding, overmolding, or the like; or other suitable attachment means. Alternatively, the proximal end of the retention wire (508) extends proximally inside the longitudinal lumen of the delivery sheath (502), and exits the proximal end of the delivery sheath (502). During an implant delivery and deployment, the end of the distal bend (510) of the retention wire (508) extends along the outer surface of the elongated implant, crosses the implant retention outlet on the implant, and reaches the retention wire cavity (512) on the delivery catheter (504).

According to one embodiment of the present teachings, the implant retention wire (408) has a locked configuration and an unlocked configuration. In its locked configuration, the distal end (510) of the retention wire (508) remains inside the wire retention cavity (512), thereby allowing the implant retention mechanism to retain the implant. In its unlocked configuration, the distal end (510) of the retention wire (508) is released from the retention wire cavity (512), thereby releasing the implant from its attachment to implant retention mechanism.

According to one embodiment of the present teachings, the retention wire cavity (512) forms an angle of 5° to 90° with the longitudinal axis of the delivery catheter (504). According to one embodiment of the present teachings, to achieve its locked configuration, the retention wire (512) is pushed slightly distally while the delivery catheter (504) remains steady, thereby keeping the distal end (510) of the retention wire (508) inside the retention wire cavity (512). In an alternative embodiment, to achieve its locked configuration, the delivery catheter (504) is pulled slightly proximally while the retention wire (512) is held steady, thereby keeping the distal end (510) of the retention wire (508) inside the retention wire cavity (512). In yet another embodiment, other means known to those skilled in the art can be used for keeping the distal end (510) of the retention wire (508) inside the retention wire cavity.

According to one embodiment of the present teachings, to achieve its unlocked configuration, the retention wire (508) is pulled proximally while the delivery catheter (504) is held steady, releasing the distal end (510) of the retention wire (508) from the retention wire cavity (512). Alternatively, to achieve its unlocked configuration, the delivery catheter (504) is pushed distally while the retention wire (508) is held steady, releasing the distal end (510) of the retention wire (508) from the retention wire cavity (512). In yet another embodiment, other means known to those skilled in the art can be used to release the distal end (510) of the retention wire (508) from the retention wire cavity (512).

As illustrated in FIG. 22, the implant retention wire (508) retains an implant at its retention outlet as the implant is deployed. As seen in this figure, since the retention wire is small and flexible in nature, the implant device, although still constrained by the delivery catheter, also has a certain degree of freedom. This embodiment allows the implant to conform to the natural anatomy of the atrial septum as much as possible while still giving the clinician the ability to pull back the implant if necessary. At this point, if a clinician decides that the implant deployment is not satisfactory, he/she can retract the entire implant retention mechanism, including the delivery catheter (504), implant retention wire (508) with its distal end (510) remaining inside the retention wire cavity (512), proximally, thereby pulling the implant proximally back into the delivery sheath (502).

Now referring to FIG. 23, when the implant is ready to be released, a clinician retracts the retention wire (508) proximally while holding the delivery catheter (504) steady, allowing the distal end (510) of the retention wire (508) to be released from the implant retention cavity (512). Alternatively, the delivery catheter (504) is pushed distally while holding the retention wire (508) steady, allowing the distal end (510) of the retention wire (508) to be released from the implant retention cavity (512). As the distal end (510) of the implant retention wire (508) is being released from the retention wire cavity (512) on the delivery catheter (504) and implant retention outlet, the implant is released from the implant retention mechanism. At this point, the delivery system along with implant retention mechanism can be removed from the body.

Similar to what has been described with reference to FIG. 20, according to an exemplary delivery system, the delivery sheath (502) includes a major longitudinal lumen for the delivery catheter (504) and a separate side retention wire lumen (506) for the retention wire (508) to be slidably disposed within. According to this exemplary delivery system, the delivery catheter (504) is slidably disposed within the major longitudinal lumen of the delivery sheath (502) and the retention wire (508) is slidably disposed within the side lumen (506). In an alternative embodiment, the delivery sheath (502) has only one longitudinal lumen where both the delivery catheter (504) and the retention wire (508) are disposed within. According to one embodiment of the present teachings, the retention wire has a size of 0.010", 0.011", 0.014", 0.018", 0.021", 0.028", 0.035", 0.038", 0.042" or 0.045". In other embodiments of the present teachings, the retention wire has a size in the range of 0.010" and 0.045".

Figure 24:
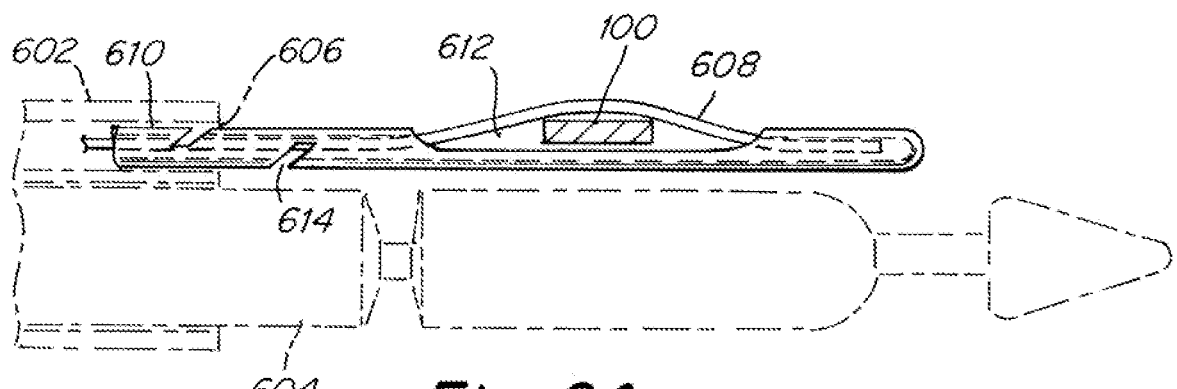
FIG. 24 is a perspective view of an exemplary implant retention mechanism attaching to a deployed medical device in accordance with the present teachings.

FIG. 24 illustrates another embodiment of the present teachings. The embodiment illustrated in FIG. 24 has a similar delivery system and implant configuration to what has been described above with reference to FIG. 20. The above-described details referring FIGS. 20-21 are therefore incorporated herein. As illustrated in FIG. 24, the implant retention wire (608) is slidably disposed within the elongated tube (610). Similar to what has been described with reference to FIG. 22, in this embodiment, the delivery sheath (602) includes a major longitudinal lumen for the delivery catheter (604) and a separate side retention wire tube lumen (606) for the retention wire tube (610) to be slidably disposed within. In an alternative embodiment, the delivery sheath (602) has only one lumen where both the delivery catheter (604) and retention wire tube (610) are disposed within. According to one embodiment of the present teachings, the retention wire tube (610) is sized to hold a retention wire of 0.010", 0.011", 0.014", 0.018", 0.021", 0.028", 0.035", 0.038", 0.042" or 0.045". In other embodiments of the present teachings, the retention tube is sized to hold a retention wire having a size in the range of 0.010" and 0.045".

In one embodiment of the present teachings, the retention wire tube (610) has a proximal end, a distal end, and an elongated longitudinal lumen for the retention wire (608) to be slidably disposed within. FIG. 24 illustrates the distal end portion of the retention wire tube (610) retaining an implant. As shown in the figure, the retention wire tube (610) has a side opening (612) near its distal end on its tubular surface. According to one embodiment, during implant delivery, the implant is stretched to an elongated delivery profile, with a proximal portion of the implant slidably disposed over a distal portion of the delivery catheter and a distal portion of the retention wire tube (610), with the implant retention outlet overlapping the side opening on the retention wire tube. The distal end of the implant retention wire (608) extends distally within the elongated lumen of the retention wire tube (610), exits the side opening (612) of the retention wire tube (610), further extends along the outer surface of the implant, crosses the implant retention outlet and back into the side opening (612) of the retention wire tube (610). The distal end of the retention wire (608) is stowed inside the elongated lumen of the retention wire tube (610) distal to the side opening (612).

According to one embodiment of the present teachings, the implant retention wire (608) also has a locked configuration and an unlocked configuration. In its locked configuration, the distal end of the retention wire (608) remains inside the elongated lumen of the retention wire tube (610) distal to the side opening (612) of the retention wire tube (610), thereby allowing the implant retention mechanism to retain the implant. In its unlocked configuration, the distal end of the retention wire (608) is released from the elongated lumen of the retention wire tube (610) distal to the side opening (612) of the retention wire tube (610), and extends outside of the side opening (612) of the retention wire tube (610), thereby releasing the implant from its attachment to the implant retention mechanism.

According to one embodiment of the present teachings, as the implant being deployed and both delivery sheath and delivery catheter being retracted, the implant is retained by the implant retention mechanism as shown in FIG. 24. As seen in this figure, since the retention wire tube is small and flexible comparing to the delivery catheter, the deployed implant therefore has a greater degree of freedom. This embodiment allows the implant to conform to the natural anatomy of the atrial septum as much as possible while still giving the clinician the ability to pull back the implant if necessary. According to other embodiments of the present teachings, a portion of the retention wire tube (610) may have cuts (614) along its tubular surface to reduce the stiffness of the retention wire tube (610) and achieve greater flexibility to the implant retention mechanism. In one embodiment, the cut could be straight, or in the shape of a spiral, or other shape and form known to skilled artisan in the field. In another embodiment, one or a series of cuts are used.

At this point, if a clinician decides that the implant deployment is not satisfactory, he/she can retract the entire implant retention mechanism, including the wire retention tube (610) and retention wire (608) in its locked configuration proximally, and pull the implant proximally back into the delivery sheath (602).

When the implant is ready to be released, a clinician retracts the retention wire (608) proximally while holding the retention wire tube (610) steady, allowing the distal end of the retention wire (608) to be released from the longitudinal lumen distal to the side opening (612) on the retention wire tube (610). Alternatively, the retention wire tube (610) is pushed distally while the retention wire (608) is held steady, allowing the distal end of the retention wire (608) to be released from the longitudinal lumen distal to the side opening (612) on the retention wire tube (610). As the distal end of the implant retention wire (608) being released from the elongated lumen of the retention wire tube (610) distal to the side opening (612) and implant retention outlet, the implant is released from the implant retention mechanism. At this point, the delivery system along with implant retention mechanism can be removed from the body.

Figure 25:
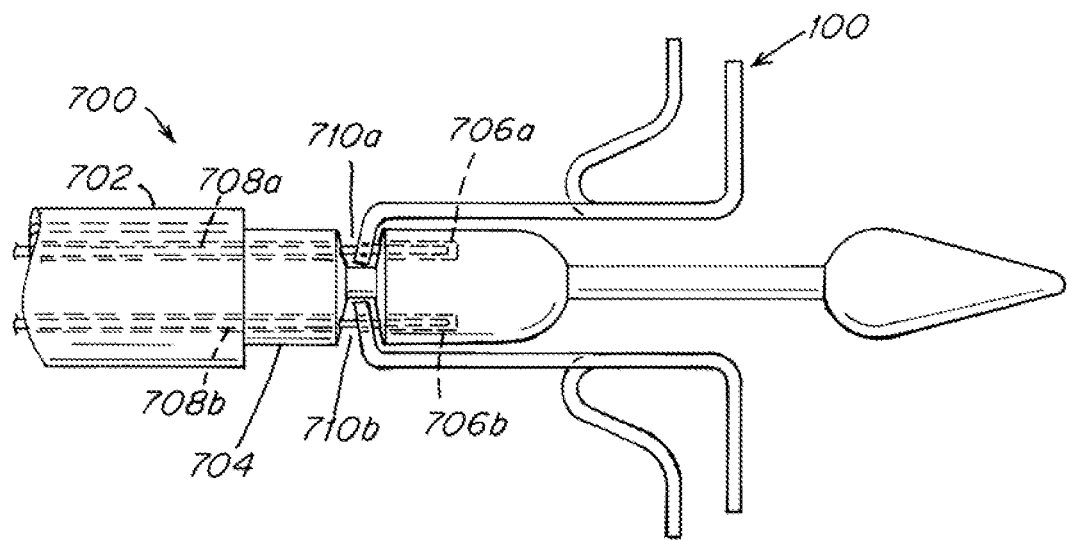
FIG. 25 is a perspective view of an exemplary medical device delivery system attaching to a deployed medical device in accordance with the present teachings.

FIG. 25 illustrates another embodiment of the present teachings. The embodiment illustrated in FIG. 25 also has a similar delivery system and implant configuration to what has been described above with reference to FIG. 20. The above-described details referring FIGS. 20-21 are therefore incorporated herein. As illustrated in FIG. 25, the delivery system (700) can include a delivery sheath (702), a delivery catheter (704), and at least one implant retention wire (708). In this exemplary system, the delivery sheath (702) has a proximal end, a distal end, and an elongated lumen extending from its proximal end to the distal end where the delivery catheter (704) is slidably disposed within. The delivery catheter (704) also has a proximal end, a distal end, and at least one elongated lumen (706) extending from its proximal end distally for the at least one implant retention wire (708) to be slidably disposed within. The delivery catheter (704) can also include at least one surface cavity (710) deep enough to intersect with the elongated lumen. In various embodiments of the present teachings, the elongated lumen (706) within the delivery catheter (704) extends from the proximal end of the delivery catheter (704) to the distal end of the delivery catheter (704). Alternatively, the elongated lumen (706) within the delivery catheter (704) extends from the proximal end of the delivery catheter (704) to a stop distal to the distal end of the delivery catheter (704). According to one embodiment of the present teachings, the elongated lumen (706) is sized to hold a retention wire (708) of 0.010", 0.011", 0.014", 0.018", 0.021", 0.028", 0.035", 0.038", 0.042" or 0.045". In other embodiments of the present teachings, the elongated lumen (706) is sized to hold a retention wire having a size in the range of 0.010" and 0.045".

According to one embodiment of the present teachings, as shown in FIG. 25, during an implant delivery and deployment, the implant is stretched to an elongated delivery profile, with a proximal portion of the implant slidably disposed over a distal portion of the delivery catheter (704), and the proximal end of this portion folds radially inward and is disposed in a surface cavity (710) of the delivery catheter (704). In one embodiment, an implant retention outlet is located on the folded proximal end portion of the implant, so that the implant retention wire (708) extends within the elongated lumen (706) of the delivery catheter (704), through the surface cavity (710) of the delivery catheter (704), crosses the implant retention outlet, and extends further into the distal end of the lumen (706).

In one embodiment of the present teachings, the implant has multiple proximal flanges, where only one flange is retained by the implant retention wire (708) through implant retention mechanism as illustrated in FIG. 25. Alternatively, the implant has multiple proximal flanges, where more than one flange is retained by the more than one implant retention wires (708) through implant retention mechanism as illustrated in FIG. 25.

In one embodiment as illustrated in FIG. 25, two implant retention wires (708) are included in the delivery system (700). In another embodiment of the present teachings, multiple implant retention wires (708) are included in the delivery system (700). In various embodiments, multiple implant retention wires (708) are evenly distributed radially across the elongated axis of the delivery catheter (704), each intersecting a surface cavity (710) on the delivery catheter (704). Alternatively, multiple implant retention wires (708) are randomly distributed radially across the elongated axis of the delivery catheter (704), each intersecting a surface cavity (710) on the delivery catheter (704).

According to one embodiment of the present teachings, the implant retention wire (708) has a locked configuration and an unlocked configuration. In its locked configuration, the distal portion of the retention wire (708) extends through the surface cavity (710) intersecting the elongated lumen (706) and the implant retention outlet, thereby allowing the implant retention mechanism to retain the implant. In its unlocked configuration, the distal portion of the retention wire (708) retracts proximally from the implant retention outlet, and the surface cavity (710) intersecting the elongated lumen (706), thereby releasing the implant from its attachment to implant retention mechanism.

According to one embodiment of the present teachings, after the implant being deployed, the implant is retained by the implant retention mechanism as shown in FIG. 25. As seen in this figure, a small portion of the implant is retained by the retention wire (708) and the rest portion of the implant conforms to the natural anatomy of the atrial septum. At this point, if a clinician decides that the implant deployment is not satisfactory, he/she can retract the entire implant retention mechanism, including delivery catheter along with the implant retention wire in its locked configuration proximally, thereby pull the implant proximally back into the delivery sheath (702).

Figure 26:
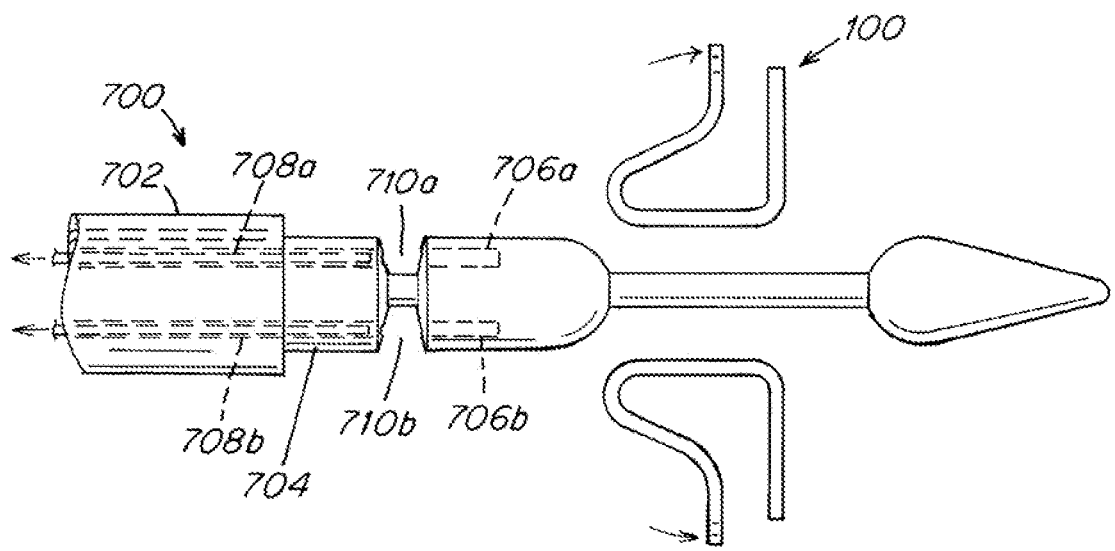
FIG. 26 is a perspective view of an exemplary medical device delivery system in FIG. 25 releasing a deployed medical device in accordance with the present teachings.

Now referring to FIG. 26, when the implant is ready to be released, a clinician retracts the retention wire (708) proximally while holding the delivery catheter (704) steady, allowing the distal end (710) of the retention wire (708) extend proximally to the surface cavity (710) of the delivery catheter (704) and release the implant retention outlet. Alternatively, the delivery catheter (704) is pushed distally while holding the retention wire (708), thereby releasing the retention wire (708) from the implant retention outlet. Upon doing so, the implant is released completely. At this point, the delivery system along with implant retention mechanism can be removed from the body.

The methods and devices disclosed above are useful for treating symptoms of left heart failures, in particular diastolic heart failures, by reducing the pressure in the left atrium and pulmonary veins. Specific details are disclosed which would allow one with ordinary skill in the art to make and use the devices and practice the methods according to the present teachings. One skilled in the art will further recognize that devices according to the present teachings could be used to regulate pressure in other parts of the heart and/or vascular portions of the body. The methods and devices disclosed above are also useful for treating congenital heart disease such as ASD, VSD, or PFO.

Various embodiments have been illustrated and described herein by way of examples, and one of skill in the art will appreciate that variations can be made without departing from the spirit and scope of the present teachings. The present teachings are capable of other embodiments or of being practiced or carried out in various ways. Also, it is to be understood that the phraseology and terminology employed herein is for the purpose of description and should not be regarded as limiting.

As used herein, the term "catheter" or "sheath" encompasses any hollow instrument capable of penetrating body tissue or interstitial cavities and providing a conduit for selectively injecting a solution or gas. The term "catheter" or "sheath" is also intended to encompass any elongate body capable of serving as a conduit for one or more of the ablation, expandable or sensing elements. Specifically, in the context of coaxial instruments, the term "catheter" or "sheath" can encompass either the outer catheter body or sheath or other instruments that can be introduced through such a sheath. The use of the term "catheter" should not be construed as meaning only a single instrument but rather is used to encompass both singular and plural instruments, including coaxial, nested, and other tandem arrangements. Moreover, the terms "sheath" or "catheter" are sometime used interchangeably to describe catheters having at least one lumen through which instruments or treatment modalities can pass.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, controls. In addition, the materials, methods, and examples described above are illustrative only and not intended to be limiting.

While the description above refers to strings, filaments, sutures and wires and the term "wire" might convey a more rigid piece than a string, a suture or a filament, all these terms are essentially interchangeable and further include embodiments in which the wire, string, suture or filament is a hollow tube or conduit to allow another wire, as needed, to pass through its longitudinal axis. Each wire, string, suture and filament can comprise one or more wires, strings, sutures and filaments.

In cases in which the device is made of a polymer, it can be desirable to add an additive or coating to the material to make it radiopaque or to make it more visible in a wider variety of imaging techniques.

It will be appreciated that while a particular sequence of steps has been shown and described for purposes of explanation, the sequence may be varied in certain respects or the steps may be combined.

We claim:

1. A delivery system comprising a delivery sheath, a delivery catheter, and an implant retention mechanism,
    wherein the delivery sheath comprises a proximal end, a distal end, and an elongated lumen extending from the proximal end to the distal end of the delivery sheath;
    wherein the delivery catheter is slidably disposed within the delivery sheath, and the delivery catheter comprises a proximal end, a distal end, and at least one elongated lumen extending from the proximal end to the distal end of the delivery catheter, and a retention wire cavity on an outer surface of the delivery catheter;
    wherein the implant retention mechanism comprises an implant retention wire having a fixed end attaching to the delivery catheter and a free end; and
    wherein the implant retention wire has at least two configurations, a first configuration wherein the free end of the implant retention wire is secured inside the retention wire cavity between an inner surface of the delivery sheath and the outer surface of the delivery catheter, and a second configuration where the free end of the implant retention wire is released from the wire retention cavity and is distal to the distal end of the delivery catheter, and the implant retention wire assumes a relatively straight profile wherein the free end is distal to the fixed end.

2. The delivery system of claim 1, wherein the fixed end of the implant retention wire attaches to a distal end portion of the delivery catheter.

3. The delivery system of claim 1, wherein in its first configuration, the free end of the implant retention wire extends distally from the distal end of the delivery catheter, crosses an implant device, and extends back proximally beyond the distal end of the delivery catheter and is secured inside the retention wire cavity between the inner surface of the delivery sheath and the outer surface of the delivery catheter.

4. The delivery system of claim 1, wherein the implant retention wire has an elasticity or a shape memory which allows the implant retention wire to resume a relatively straight profile in its second configuration.

5. The delivery system of claim 1, wherein the implant retention wire in its first configuration engages an implant.

6. The delivery system of claim 1, wherein the implant retention wire in its second configuration releases an implant.

7. The delivery system of claim 1, wherein in its first configuration, the delivery sheath slides over the wire retention cavity on the delivery catheter and thereby secures the free end of the implant retention wire inside the wire retention cavity.

* * * * *